US009994621B2

(12) United States Patent
Gossele et al.

(10) Patent No.: US 9,994,621 B2
(45) Date of Patent: Jun. 12, 2018

(54) GENES ENCODING INSECTICIDAL PROTEINS

(75) Inventors: Veronique Gossele, Ghent (BE); Frank Meulewaeter, Merelbeke (BE); Bernadette Saey, Evergem (BE); Stefan Jansens, Ghent (BE)

(73) Assignee: BAYER CROPSCIENCE N.V., Diegem (BE)

( * ) Notice: Subject to any disclaimer, the term of this patent is extended or adjusted under 35 U.S.C. 154(b) by 1916 days.

(21) Appl. No.: 12/602,327

(22) PCT Filed: May 28, 2008

(86) PCT No.: PCT/EP2008/004550

§ 371 (c)(1),
(2), (4) Date: Nov. 30, 2009

(87) PCT Pub. No.: WO2008/145406

PCT Pub. Date: Dec. 4, 2008

(65) Prior Publication Data

US 2010/0180351 A1 Jul. 15, 2010

Related U.S. Application Data

(60) Provisional application No. 60/934,367, filed on Jun. 13, 2007.

(30) Foreign Application Priority Data

Jun. 1, 2007 (EP) .................................... 07010872

(51) Int. Cl.
*C07K 14/325* (2006.01)
*C12N 15/32* (2006.01)
*C12N 15/82* (2006.01)

(52) U.S. Cl.
CPC ........ *C07K 14/325* (2013.01); *C12N 15/8285* (2013.01); *C12N 15/8286* (2013.01); *Y02A 40/164* (2018.01)

(58) Field of Classification Search
CPC .......................... C12N 15/8286; C07K 14/325
See application file for complete search history.

(56) References Cited

U.S. PATENT DOCUMENTS

| | | | | |
|---|---|---|---|---|
| 4,407,956 A | 10/1983 | Howell | | |
| 4,536,475 A | 8/1985 | Anderson | | |
| 4,684,611 A | 8/1987 | Schilperoort et al. | | |
| 5,254,799 A | 10/1993 | DeGreve et al. | | |
| 5,510,471 A | 4/1996 | Lebrun et al. | | |
| 5,635,618 A | 6/1997 | Capellades et al. | | |
| 6,033,874 A | 3/2000 | Baum et al. | | |
| 6,140,553 A | 10/2000 | D'Halluin | | |
| 6,204,246 B1 * | 3/2001 | Bosch et al. | 514/4.5 | |
| 7,049,491 B2 * | 5/2006 | Jansens et al. | 800/302 | |
| 7,501,559 B2 * | 3/2009 | Van Mellaert et al. | 800/302 | |
| 2003/0167517 A1 | 9/2003 | Arnaut et al. | | |
| 2005/0097633 A1 * | 5/2005 | Diehn et al. | 800/278 | |
| 2010/0024075 A1 | 1/2010 | Aroian et al. | | |
| 2010/0235951 A1 | 9/2010 | Van Rie et al. | | |
| 2017/0107534 A1 | 4/2017 | Van Rie et al. | | |

FOREIGN PATENT DOCUMENTS

| | | |
|---|---|---|
| CN | 1840655 | 10/2006 |
| EP | 0 067 553 | 5/1982 |
| EP | 0 116 718 | 12/1983 |
| EP | 0 193 259 | 9/1986 |
| EP | 0 233 247 | 8/1987 |
| EP | 0 242 246 | 10/1987 |
| EP | 0 270 822 | 6/1988 |
| EP | 0270 356 | 6/1988 |
| EP | 0 408 403 | 1/1991 |
| WO | WO 84/02913 | 8/1984 |
| WO | WO 85/01856 | 5/1985 |
| WO | WO 90/06999 | 6/1990 |
| WO | WO 92/09696 | 6/1992 |
| WO | WO 96/06932 | 3/1996 |
| WO | WO 98/15630 | 4/1998 |
| WO | WO 00/26371 | 5/2000 |
| WO | WO 00/71733 | 11/2000 |
| WO | WO 01/02579 | 1/2001 |
| WO | WO 02/057664 | 7/2002 |
| WO | WO 07/107302 | 9/2007 |

OTHER PUBLICATIONS

MacDonald et al (Nucleic Acid Research (vol. 19) 1994 p. 5575-5581.*
Friedberg (Brief. Bioinformatics (2006) 7: 225-242).*
McElroy et al (The Plant Cell, vol. 2 163-171, Feb. 1990, p. 163-171.*
Tang et al (Mol Breeding 2006, p. 1-10).*
Goff et al (Science (2002) vol. 296, p. 96-100).*
Kota et al (PNAS vol. 96 pp. 1840-1845) 1999).*
Van den Broeck (Nature, vol. 313, Jan. 1985, p. 358-363).*
Zhao et al (Journal of Economic Entomology, 94(6):1547-1552. 2001).*
Nakamura et al (Nucl. Acids Res. 2000 28, 292).*
Castle et al (Current Opinion in Biotechnology 2006, 17:105-112).*
Callis et al (Genes & Development 1:1183-1200 1987).*
Alcantara et al., (2004) Archives of Insect Biochemistry and Physiology, vol. 55, No. 4, pp. 169-177.
An et al., (1996) Plant Journal, vol. 10, pp. 107-121.
Bernhard and Utz (1993), Bacillus Thuringiensis, An Environmental Biopesticide: Theory and Practice, pp. 255-267.
Boevink et al., (1995) Virology, vol. 207, pp. 354-361.
Bradford et al., (1976) Anal. Biochem., vol. 72, pp. 248-254.
Breitler et al., (2001) Molecular Breeding, vol. 7, pp. 259-274.
Brown, (1986) Nucleic Acids Res., vol. 14, pp. 9549-9559.
Brown and Simpson, (1998) Ann. Rev. Plant Physiol. Plant Mol. Biol., vol. 49, pp. 77-95.
Brown et al., (1996) Plant Mol Biol., vol. 32, pp. 531-535.
Cao et al., (1999), Molecular Breeding, vol. 5, pp. 131-141.
Cao et al., (2002) Theoretical and Applied. Genetics, vol. 105, No. 2-3, pp. 258-264.

(Continued)

*Primary Examiner* — Lee A Visone
(74) *Attorney, Agent, or Firm* — Arent Fox LLP

(57) ABSTRACT

The present invention relates to novel DNA sequences encoding insecticidal Cry1 C proteins derived from *Bacillus thuringiensis*, and their use in plants to control insect pests. Also included herein are plant cells or plants comprising such genes and methods of making or using them, as well as plant cells or plants comprising a Cry1 C chimeric gene of the invention and at least one other chimeric gene, such as a chimeric gene encoding an insecticidal Cry1Ab protein, and methods of making or using such plant cells or plants.

43 Claims, No Drawings

(56) References Cited

OTHER PUBLICATIONS

Cheng et al., (1998) Proc Natl Acad Sci USA, vol. 95, pp. 2767-2772.
Christensen et al., (1992) Plant Mol. Biol., vol. 18, pp. 675-689.
Christou et al., (1990) Trends Biotechnology, vol. 8, pp. 145-151.
Cordero et al., (1994) The Plant Journal, vol. 6, pp. 141-150.
Cornejo et al., (1993) Plant Mol. Biol., vol. 23, pp. 567-581.
Cornelissen & Vandewiele, (1989) Nucleic Acids Research, vol. 17, pp. 19-29.
Crickmore et al., (1998) Microbiol. Mol. Biol. Rev., vol. 62, No. 3, pp. 807-813.
Deblaere et al., (1985) Nucl. Acids Res., vol. 13, pp. 4777-4788.
De Block et al., (1989) Plant Physiology, vol. 91, pp. 694-701.
De Greve et al., (1983) Journal. of. Mol. Appl. Genetics, vol. 1, No. 6, pp. 499-511.
Dennis et al., (1984) Nucleic Acids Res., vol. 12, No. 9, pp. 3983-4000.
De Pater et al., (1992), Plant Journal, vol. 2, pp. 837-844.
Depicker et al., (1982) Journal of Molecular and Applied Genetics, vol. 1, pp. 561-573.
Duan et al., (1996) Nature Bio/Technology, vol. 14, pp. 494-498.
Dulmage, (1981) Biological Control in Crop Production, pp. 129-141.
Eckes et al., (1986) Molecular and General Genetics, vol. 205, pp. 14-22.
Estruch et al., (1996) Proc. Natl. Acad Sci USA, vol. 93, pp. 5389-5394.
Ffrench-Constant and Bowen, (2000) Cell Mol Life Sci., vol. 57, pp. 828-833.
Franck et al., (1980) Cell, vol. 21, pp. 285-294.
Fromm et al., (1990) Bio/Technology, vol. 8, pp. 833-839.
Fujimoto et al., (1993) Biotechnology, vol. 11, No. 10, pp. 1151-1155.
Gardner et al., (1981) Nucleic Acids Research, vol. 9, pp. 2871-2887.
Ghareyazie et al., (1997) Molecular Breeding, vol. 3, pp. 401-414.
Gielen et al., (1984) Embo Journal, vol. 3, pp. 835-845.
Gordon-Kamm et al., (1990) The Plant Cell, vol. 2, pp. 603-618.
Hinchee et al., (1988) Bio/Technology, vol. 6, pp. 915-922.
Ho et al., (2006) Crop Science, vol. 46, pp. 781-789.
Hofte et al., (1988) Appl. and Environm. Microbiol. vol. 54, pp. 2010-2017.
Hull and Howell, (1978) Virology, vol. 86, pp. 482-493.
Itoh et al., (1984) Plasmid, vol. 11, pp. 206-220.
Jansens et al., (1997) Crop Science, vol. 37, pp. 1616-1624.
Last et al., (1990) Theor. Appl. Genet., vol. 81, pp. 581-588.
Mahillon et al. (1989), FEMS Microbiol. Letters, vol. 60, pp. 205-210.
Marshall et al. (1996) Plant Physiology, vol. 111, pp. 1251-1261.
Maqbool et al., (1998) Molecular Breeding, vol. 4, pp. 501-507.
McElroy et al. (1990) Plant Cell, vol. 2, pp. 163-171.
Nayak et al. (1997) Proc. Natl. Acad. Sci. USA, vol. 94, pp. 2111-2116.
Needleman and Wunsch (1970) J. Mol. Biol., vol. 48: pp. 443-453.
Odell et al. (1985) Nature, vol. 313: pp. 810-812.
Oelmuller et al. (1993), Mol. Gen. Genet., vol. 237, pp. 261-272.
Rao et al. (1998) Plant Journal, vol. 15, No. 4, pp. 469-477.
Rice et al. (2000) Trends in Genetics, vol. 16, pp. 276-277.
Shcherban et al. (1995) Proc. Natl. Acad. Sci. USA, vol. 92, pp. 9245-9249.
Stanssens at al. (1989) Nucleic Acids Research, vol. 12, pp. 4441-4454.
Strizhov et al. (1996) Proc. Natl. Acad. Sci., vol. 93: pp. 15012-15017.
Tang et al. (2006) Molecular Breeding, vol. 18, pp. 1-10.
Thompson et al. (1987) The EMBO Journal, vol. 6, pp. 2519-2523.
Vandersalm et al. (1994) Plant Molecular Biology, vol. 26, No. 1, pp. 51-59.
Van Den Sroeck et al. (1985) Nature, vol. 313, pp. 358-363.
Van Rie et al. (1990) Science, vol. 247, pp. 72-74.
Velten et al. (1984) EMSO Journal, vol. 3, pp. 2723-2730.
Velten and Schell (1985) Nucleic Acids Research, vol. 13, pp. 6981-6998.
Verdaguer et al. (1998) Plant Mol. Biol., vol. 37, pp. 1055-1067.
Waterfield et al. (2001) Trends Microbial, vol. 9, pp. 185-191.
White et al. (1989) Trends in Genet., vol. 5, pp. 185-189.
Wong et al. (1992) Plant Molec. Biol., vol. 20, pp. 81-93.
Wu et al., (1997) Plant Cell Reports, vol. 17, pp. 129-132.
Wunn et al. (1996) Biotechnology, vol. 4, No. 2, pp. 171-176.
Zhang et al. (1991) The Plant Cell vol. 3, pp. 1155-1165.
Zhao et al. (2003) Nature Biotechnology, vol. 21: pp. 1493-1497.
Genbank Accession No. X04049, Nov. 14, 2006.
Genbank Accession No. X78988, Apr. 18, 2005.
Mascarenhas et al., "Intron-mediated enhancement of heterologous gene expression in maize," Plant Molecular Biology, vol. 15, 1990, pp. 913-920.
Pang et al., "An Improved Green Fluorescent Protein Gene as a Vital Marker in Plants," Plant Physiol., vol. 112, 1996, pp. 893-900.
Rose, "The effect of intron location on intron-mediated enhancement of gene expression in *Arabidopsis*," The Plant Journal, 2004, vol. 40, pp. 744-751.
Zhao et al., "Concurrent use of transgenic plants expressing a single and two Bacillus thuringiensis genes speeds insect adaptation to pyramided plants," PNAS, vol. 102(24), Jun. 2005, pp. 8426-8430.

* cited by examiner

SEQUENCE LISTING

```
<160> NUMBER OF SEQ ID NOS: 14

<210> SEQ ID NO 1
<211> LENGTH: 2418
<212> TYPE: DNA
<213> ORGANISM: Artificial Sequence
<220> FEATURE:
<223> OTHER INFORMATION: synthetic sequence
<220> FEATURE:
<221> NAME/KEY: CDS
<222> LOCATION: (1)..(590)
<220> FEATURE:
<221> NAME/KEY: Intron
<222> LOCATION: (591)..(1124)
<220> FEATURE:
<221> NAME/KEY: CDS
<222> LOCATION: (1125)..(2415)

<400> SEQUENCE: 1

atg gag gag aac aac cag aac caa tgc atc ccg tac aat tgc ctc agc        48
Met Glu Glu Asn Asn Gln Asn Gln Cys Ile Pro Tyr Asn Cys Leu Ser
1               5                   10                  15

aat ccc gaa gag gtg ctc ctt gac gga gag agg atc tca acc ggg aac        96
Asn Pro Glu Glu Val Leu Leu Asp Gly Glu Arg Ile Ser Thr Gly Asn
            20                  25                  30

agt tcc atc gac atc agc ttg agt ctc gtt cag ttc ctc gtg agc aac       144
Ser Ser Ile Asp Ile Ser Leu Ser Leu Val Gln Phe Leu Val Ser Asn
        35                  40                  45

ttc gtg cct gga ggg gga ttt ctc gtg ggt ctc atc gac ttt gtg tgg       192
Phe Val Pro Gly Gly Gly Phe Leu Val Gly Leu Ile Asp Phe Val Trp
    50                  55                  60

ggt ata gtt gga ccg agt caa tgg gac gcc ttt ctc gtt cag atc gag       240
Gly Ile Val Gly Pro Ser Gln Trp Asp Ala Phe Leu Val Gln Ile Glu
65                  70                  75                  80

cag ctc atc aac gag agg att gcc gag ttt gca agg aat gcc gca ata       288
Gln Leu Ile Asn Glu Arg Ile Ala Glu Phe Ala Arg Asn Ala Ala Ile
                85                  90                  95

gca aac ctc gaa ggt ctc ggc aac aac ttc aac atc tac gtc gaa gcg       336
Ala Asn Leu Glu Gly Leu Gly Asn Asn Phe Asn Ile Tyr Val Glu Ala
            100                 105                 110

ttc aag gag tgg gag gaa gac cct aac aac cca gag aca agg aca agg       384
Phe Lys Glu Trp Glu Glu Asp Pro Asn Asn Pro Glu Thr Arg Thr Arg
        115                 120                 125

gtg atc gac agg ttc agg atc ctt gac gga ctt ctc gaa cgc gac att       432
Val Ile Asp Arg Phe Arg Ile Leu Asp Gly Leu Leu Glu Arg Asp Ile
    130                 135                 140
```

-continued

```
ccg agc ttc aga atc agc gga ttc gaa gtc cct ttg ctc tct gtg tac      480
Pro Ser Phe Arg Ile Ser Gly Phe Glu Val Pro Leu Leu Ser Val Tyr
145                 150                 155                 160

gcc caa gct gcc aat ctc cac ctc gct atc ctc aga gac agc gtg atc      528
Ala Gln Ala Ala Asn Leu His Leu Ala Ile Leu Arg Asp Ser Val Ile
                165                 170                 175

ttc gga gaa aga tgg gga ctc act acc atc aac gtg aac gag aac tac      576
Phe Gly Glu Arg Trp Gly Leu Thr Thr Ile Asn Val Asn Glu Asn Tyr
            180                 185                 190

aac agg ctc ata ag  gtccgccttg tttctcctct gtctcttgat ctgactaatc      630
Asn Arg Leu Ile Arg
        195

ttggtttatg attcgttgag taattttggg gaaagcttcg tccacagttt ttttttcgat    690

gaacagtgcc gcagtggcgc tgatcttgta tgctatcctg caatcgtggt gaacttatgt    750

cttttatatc cttcactacc atgaaaagac tagtaatctt tctcgatgta acatcgtcca    810

gcactgctat taccgtgtgg tccatccgac agtctggctg aacacatcat acgatattga    870

gcaaagatct atcttccctg ttctttaatg aaagacgtca ttttcatcag tatgatctaa    930

gaatgttgca acttgcaagg aggcgtttct ttctttgaat ttaactaact cgttgagtgg    990

ccctgtttct cggacgtaag gcctttgctg ctccacacat gtccattcga attttaccgt   1050

gtttagcaag ggcgaaaagt ttgcatcttg atgatttagc ttgactatgc gattgctttc   1110

ctggacccgt gcag g cac atc gac gag tac gcc gat cac tgt gcg aac acc   1161
                  His Ile Asp Glu Tyr Ala Asp His Cys Ala Asn Thr
                      200                 205

tac aac cgg gga ctc aac aac ctt ccc aag tct acc tac caa gat tgg     1209
Tyr Asn Arg Gly Leu Asn Asn Leu Pro Lys Ser Thr Tyr Gln Asp Trp
210                 215                 220                 225

atc acc tac aac cgt ctc cgg aga gat ctt acc ctc act gtt ctc gat     1257
Ile Thr Tyr Asn Arg Leu Arg Arg Asp Leu Thr Leu Thr Val Leu Asp
                230                 235                 240

atc gca gct ttc ttc ccc aac tac gac aac agg aga tac ccg ata caa     1305
Ile Ala Ala Phe Phe Pro Asn Tyr Asp Asn Arg Arg Tyr Pro Ile Gln
            245                 250                 255

ccc gtt gga caa ctc acg aga gag gtg tac acc gat cca ctc atc aac     1353
Pro Val Gly Gln Leu Thr Arg Glu Val Tyr Thr Asp Pro Leu Ile Asn
        260                 265                 270

ttc aac cct cag ctt caa agc gtg gca cag ctt cct acc ttc aac gtg     1401
Phe Asn Pro Gln Leu Gln Ser Val Ala Gln Leu Pro Thr Phe Asn Val
    275                 280                 285

atg gag tcc tca gcg ata agg aac cct cat ctc ttc gac atc ctg aac     1449
Met Glu Ser Ser Ala Ile Arg Asn Pro His Leu Phe Asp Ile Leu Asn
290                 295                 300                 305

aac ctc acc atc ttc acc gac tgg ttt agt gtg ggc agg aac ttc tac     1497
Asn Leu Thr Ile Phe Thr Asp Trp Phe Ser Val Gly Arg Asn Phe Tyr
                310                 315                 320

tgg gga ggc cac aga gtg atc agc tca ctc att ggc gga ggg aac atc     1545
Trp Gly Gly His Arg Val Ile Ser Ser Leu Ile Gly Gly Gly Asn Ile
            325                 330                 335

acc tca ccc atc tat ggc aga gaa gcg aat caa gaa cct ccg agg agt     1593
Thr Ser Pro Ile Tyr Gly Arg Glu Ala Asn Gln Glu Pro Pro Arg Ser
        340                 345                 350

ttc acc ttc aac gga ccg gtc ttc aga acc ttg agc aac cct aca ctc     1641
Phe Thr Phe Asn Gly Pro Val Phe Arg Thr Leu Ser Asn Pro Thr Leu
    355                 360                 365

aga ctc ctc cag caa cca tgg cca gca ccg cca ttc aac ctc aga ggc     1689
Arg Leu Leu Gln Gln Pro Trp Pro Ala Pro Pro Phe Asn Leu Arg Gly
370                 375                 380                 385
```

```
gtg gaa ggc gtg gag ttc tct acg cca acc aac tcc ttc acg tac aga      1737
Val Glu Gly Val Glu Phe Ser Thr Pro Thr Asn Ser Phe Thr Tyr Arg
                390                 395                 400

gga aga gga acc gtc gat tct ctc aca gaa ctg cct cca gag gac aac      1785
Gly Arg Gly Thr Val Asp Ser Leu Thr Glu Leu Pro Pro Glu Asp Asn
            405                 410                 415

tcc gtt cct ccg aga gaa ggc tat agc cac aga ctt tgc cac gcc act      1833
Ser Val Pro Pro Arg Glu Gly Tyr Ser His Arg Leu Cys His Ala Thr
        420                 425                 430

ttc gtg cag aga agt ggc acg cca ttc ctc act aca ggc gtg gtg ttc      1881
Phe Val Gln Arg Ser Gly Thr Pro Phe Leu Thr Thr Gly Val Val Phe
    435                 440                 445

agc tgg act cat agg agt gca aca ctc acc aac acg att gac cca gaa      1929
Ser Trp Thr His Arg Ser Ala Thr Leu Thr Asn Thr Ile Asp Pro Glu
450                 455                 460                 465

cgc atc aac cag ata cca ctc gtc aag gga ttc agg gtg tgg ggt ggg      1977
Arg Ile Asn Gln Ile Pro Leu Val Lys Gly Phe Arg Val Trp Gly Gly
                470                 475                 480

aca tca gtc atc act gga cca ggc ttc acc ggc ggc gac att ctc cgt      2025
Thr Ser Val Ile Thr Gly Pro Gly Phe Thr Gly Gly Asp Ile Leu Arg
            485                 490                 495

agg aac acc ttt ggc gac ttt gtg agc ctc caa gtc aac atc aac tct      2073
Arg Asn Thr Phe Gly Asp Phe Val Ser Leu Gln Val Asn Ile Asn Ser
        500                 505                 510

ccg att acc cag agg tat agg ctc agg ttc agg tat gcc tca tcg aga      2121
Pro Ile Thr Gln Arg Tyr Arg Leu Arg Phe Arg Tyr Ala Ser Ser Arg
    515                 520                 525

gat gcc aga gtg atc gtg ctc aca ggg gct gcc agt act ggc gtg gga      2169
Asp Ala Arg Val Ile Val Leu Thr Gly Ala Ala Ser Thr Gly Val Gly
530                 535                 540                 545

ggc cag gtg agt gtg aac atg cca ctc cag aag acc atg gag att ggc      2217
Gly Gln Val Ser Val Asn Met Pro Leu Gln Lys Thr Met Glu Ile Gly
                550                 555                 560

gag aac ctc act tca agg acc ttc cgc tat acg gac ttc tcc aac cca      2265
Glu Asn Leu Thr Ser Arg Thr Phe Arg Tyr Thr Asp Phe Ser Asn Pro
            565                 570                 575

ttc agc ttc agg gca aac cca gac atc atc ggc ata tca gag caa cca      2313
Phe Ser Phe Arg Ala Asn Pro Asp Ile Ile Gly Ile Ser Glu Gln Pro
        580                 585                 590

ctc ttt gga gct gga agc atc agt tca ggc gaa ctc tac atc gac aag      2361
Leu Phe Gly Ala Gly Ser Ile Ser Ser Gly Glu Leu Tyr Ile Asp Lys
    595                 600                 605

atc gag atc atc ctt gct gac gca act ttc gag gct gaa agc gac ctt      2409
Ile Glu Ile Ile Leu Ala Asp Ala Thr Phe Glu Ala Glu Ser Asp Leu
610                 615                 620                 625

gaa agg tga                                                          2418
Glu Arg
```

<210> SEQ ID NO 2
<211> LENGTH: 627
<212> TYPE: PRT
<213> ORGANISM: Artificial Sequence
<220> FEATURE:
<223> OTHER INFORMATION: Synthetic Construct

<400> SEQUENCE: 2

```
Met Glu Glu Asn Asn Gln Asn Gln Cys Ile Pro Tyr Asn Cys Leu Ser
1               5                   10                  15

Asn Pro Glu Glu Val Leu Leu Asp Gly Glu Arg Ile Ser Thr Gly Asn
            20                  25                  30
```

-continued

```
Ser Ser Ile Asp Ile Ser Leu Ser Leu Val Gln Phe Leu Val Ser Asn
        35                  40                  45

Phe Val Pro Gly Gly Gly Phe Leu Val Gly Leu Ile Asp Phe Val Trp
    50                  55                  60

Gly Ile Val Gly Pro Ser Gln Trp Asp Ala Phe Leu Val Gln Ile Glu
65                  70                  75                  80

Gln Leu Ile Asn Glu Arg Ile Ala Glu Phe Ala Arg Asn Ala Ala Ile
                85                  90                  95

Ala Asn Leu Glu Gly Leu Gly Asn Asn Phe Asn Ile Tyr Val Glu Ala
            100                 105                 110

Phe Lys Glu Trp Glu Glu Asp Pro Asn Asn Pro Glu Thr Arg Thr Arg
        115                 120                 125

Val Ile Asp Arg Phe Arg Ile Leu Asp Gly Leu Leu Glu Arg Asp Ile
    130                 135                 140

Pro Ser Phe Arg Ile Ser Gly Phe Glu Val Pro Leu Leu Ser Val Tyr
145                 150                 155                 160

Ala Gln Ala Ala Asn Leu His Leu Ala Ile Leu Arg Asp Ser Val Ile
                165                 170                 175

Phe Gly Glu Arg Trp Gly Leu Thr Thr Ile Asn Val Asn Glu Asn Tyr
            180                 185                 190

Asn Arg Leu Ile Arg His Ile Asp Glu Tyr Ala Asp His Cys Ala Asn
        195                 200                 205

Thr Tyr Asn Arg Gly Leu Asn Asn Leu Pro Lys Ser Thr Tyr Gln Asp
    210                 215                 220

Trp Ile Thr Tyr Asn Arg Leu Arg Arg Asp Leu Thr Leu Thr Val Leu
225                 230                 235                 240

Asp Ile Ala Ala Phe Phe Pro Asn Tyr Asp Asn Arg Arg Tyr Pro Ile
                245                 250                 255

Gln Pro Val Gly Gln Leu Thr Arg Glu Val Tyr Thr Asp Pro Leu Ile
            260                 265                 270

Asn Phe Asn Pro Gln Leu Gln Ser Val Ala Gln Leu Pro Thr Phe Asn
        275                 280                 285

Val Met Glu Ser Ser Ala Ile Arg Asn Pro His Leu Phe Asp Ile Leu
    290                 295                 300

Asn Asn Leu Thr Ile Phe Thr Asp Trp Phe Ser Val Gly Arg Asn Phe
305                 310                 315                 320

Tyr Trp Gly Gly His Arg Val Ile Ser Ser Leu Ile Gly Gly Gly Asn
                325                 330                 335

Ile Thr Ser Pro Ile Tyr Gly Arg Glu Ala Asn Gln Glu Pro Pro Arg
            340                 345                 350

Ser Phe Thr Phe Asn Gly Pro Val Phe Arg Thr Leu Ser Asn Pro Thr
        355                 360                 365

Leu Arg Leu Leu Gln Gln Pro Trp Pro Ala Pro Pro Phe Asn Leu Arg
    370                 375                 380

Gly Val Glu Gly Val Glu Phe Ser Thr Pro Thr Asn Ser Phe Thr Tyr
385                 390                 395                 400

Arg Gly Arg Gly Thr Val Asp Ser Leu Thr Glu Leu Pro Pro Glu Asp
                405                 410                 415

Asn Ser Val Pro Pro Arg Glu Gly Tyr Ser His Arg Leu Cys His Ala
            420                 425                 430

Thr Phe Val Gln Arg Ser Gly Thr Pro Phe Leu Thr Thr Gly Val Val
        435                 440                 445
```

-continued

```
Phe Ser Trp Thr His Arg Ser Ala Thr Leu Thr Asn Thr Ile Asp Pro
    450                 455                 460

Glu Arg Ile Asn Gln Ile Pro Leu Val Lys Gly Phe Arg Val Trp Gly
465                 470                 475                 480

Gly Thr Ser Val Ile Thr Gly Pro Gly Phe Thr Gly Gly Asp Ile Leu
                485                 490                 495

Arg Arg Asn Thr Phe Gly Asp Phe Val Ser Leu Gln Val Asn Ile Asn
            500                 505                 510

Ser Pro Ile Thr Gln Arg Tyr Arg Leu Arg Phe Arg Tyr Ala Ser Ser
        515                 520                 525

Arg Asp Ala Arg Val Ile Val Leu Thr Gly Ala Ala Ser Thr Gly Val
    530                 535                 540

Gly Gly Gln Val Ser Val Asn Met Pro Leu Gln Lys Thr Met Glu Ile
545                 550                 555                 560

Gly Glu Asn Leu Thr Ser Arg Thr Phe Arg Tyr Thr Asp Phe Ser Asn
                565                 570                 575

Pro Phe Ser Phe Arg Ala Asn Pro Asp Ile Ile Gly Ile Ser Glu Gln
            580                 585                 590

Pro Leu Phe Gly Ala Gly Ser Ile Ser Ser Gly Glu Leu Tyr Ile Asp
        595                 600                 605

Lys Ile Glu Ile Ile Leu Ala Asp Ala Thr Phe Glu Ala Glu Ser Asp
    610                 615                 620

Leu Glu Arg
625


<210> SEQ ID NO 3
<211> LENGTH: 372
<212> TYPE: DNA
<213> ORGANISM: Artificial Sequence
<220> FEATURE:
<223> OTHER INFORMATION: synthetic sequence
<220> FEATURE:
<221> NAME/KEY: CDS
<222> LOCATION: (1)..(372)

<400> SEQUENCE: 3

atg gct tcg atc tcc tcc tca gtc gcg acc gtt agc cgg acc gcc cct       48
Met Ala Ser Ile Ser Ser Ser Val Ala Thr Val Ser Arg Thr Ala Pro
1               5                   10                  15

gct cag gct aac atg gtg gct ccg ttc acc ggc ctt aag tcc aac gcc       96
Ala Gln Ala Asn Met Val Ala Pro Phe Thr Gly Leu Lys Ser Asn Ala
            20                  25                  30

gcc ttc ccc acc acc aag aag gct aac gac ttc tcc acc ctt ccc agc      144
Ala Phe Pro Thr Thr Lys Lys Ala Asn Asp Phe Ser Thr Leu Pro Ser
        35                  40                  45

aac ggt gga aga gtt caa tgt atg cag gtg tgg ccg gcc tac ggc aac      192
Asn Gly Gly Arg Val Gln Cys Met Gln Val Trp Pro Ala Tyr Gly Asn
    50                  55                  60

aag aag ttc gag acg ctg tcg tac ctg ccg ccg ctg tct atg gcg ccc      240
Lys Lys Phe Glu Thr Leu Ser Tyr Leu Pro Pro Leu Ser Met Ala Pro
65                  70                  75                  80

acc gtg atg atg gcc tcg tcg gcc acc gcc gtc gct ccg ttc cag ggg      288
Thr Val Met Met Ala Ser Ser Ala Thr Ala Val Ala Pro Phe Gln Gly
                85                  90                  95

ctc aag tcc acc gcc agc ctc ccc gtc gcc cgc cgc tcc tcc aga agc      336
Leu Lys Ser Thr Ala Ser Leu Pro Val Ala Arg Arg Ser Ser Arg Ser
            100                 105                 110

ctc ggc aac gtc agc aac ggc gga agg atc cgg tgc                      372
Leu Gly Asn Val Ser Asn Gly Gly Arg Ile Arg Cys
```

115 120

<210> SEQ ID NO 4
<211> LENGTH: 124
<212> TYPE: PRT
<213> ORGANISM: Artificial Sequence
<220> FEATURE:
<223> OTHER INFORMATION: Synthetic Construct

<400> SEQUENCE: 4

```
Met Ala Ser Ile Ser Ser Ser Val Ala Thr Val Ser Arg Thr Ala Pro
1               5                   10                  15

Ala Gln Ala Asn Met Val Ala Pro Phe Thr Gly Leu Lys Ser Asn Ala
            20                  25                  30

Ala Phe Pro Thr Thr Lys Lys Ala Asn Asp Phe Ser Thr Leu Pro Ser
        35                  40                  45

Asn Gly Gly Arg Val Gln Cys Met Gln Val Trp Pro Ala Tyr Gly Asn
    50                  55                  60

Lys Lys Phe Glu Thr Leu Ser Tyr Leu Pro Pro Leu Ser Met Ala Pro
65                  70                  75                  80

Thr Val Met Met Ala Ser Ser Ala Thr Ala Val Ala Pro Phe Gln Gly
                85                  90                  95

Leu Lys Ser Thr Ala Ser Leu Pro Val Ala Arg Arg Ser Ser Arg Ser
            100                 105                 110

Leu Gly Asn Val Ser Asn Gly Gly Arg Ile Arg Cys
        115                 120
```

<210> SEQ ID NO 5
<211> LENGTH: 2787
<212> TYPE: DNA
<213> ORGANISM: Artificial Sequence
<220> FEATURE:
<223> OTHER INFORMATION: synthetic sequence
<220> FEATURE:
<221> NAME/KEY: CDS
<222> LOCATION: (1)..(959)
<220> FEATURE:
<221> NAME/KEY: Intron
<222> LOCATION: (960)..(1493)
<220> FEATURE:
<221> NAME/KEY: CDS
<222> LOCATION: (1494)..(2784)

<400> SEQUENCE: 5

```
atg gct tcg atc tcc tcc tca gtc gcg acc gtt agc cgg acc gcc cct       48
Met Ala Ser Ile Ser Ser Ser Val Ala Thr Val Ser Arg Thr Ala Pro
1               5                   10                  15

gct cag gct aac atg gtg gct ccg ttc acc ggc ctt aag tcc aac gcc       96
Ala Gln Ala Asn Met Val Ala Pro Phe Thr Gly Leu Lys Ser Asn Ala
            20                  25                  30

gcc ttc ccc acc acc aag aag gct aac gac ttc tcc acc ctt ccc agc      144
Ala Phe Pro Thr Thr Lys Lys Ala Asn Asp Phe Ser Thr Leu Pro Ser
        35                  40                  45

aac ggt gga aga gtt caa tgt atg cag gtg tgg ccg gcc tac ggc aac      192
Asn Gly Gly Arg Val Gln Cys Met Gln Val Trp Pro Ala Tyr Gly Asn
    50                  55                  60

aag aag ttc gag acg ctg tcg tac ctg ccg ccg ctg tct atg gcg ccc      240
Lys Lys Phe Glu Thr Leu Ser Tyr Leu Pro Pro Leu Ser Met Ala Pro
65                  70                  75                  80

acc gtg atg atg gcc tcg tcg gcc acc gcc gtc gct ccg ttc cag ggg      288
Thr Val Met Met Ala Ser Ser Ala Thr Ala Val Ala Pro Phe Gln Gly
                85                  90                  95
```

```
ctc aag tcc acc gcc agc ctc ccc gtc gcc cgc cgc tcc tcc aga agc      336
Leu Lys Ser Thr Ala Ser Leu Pro Val Ala Arg Arg Ser Ser Arg Ser
            100                 105                 110

ctc ggc aac gtc agc aac ggc gga agg atc cgg tgc gag gag aac aac      384
Leu Gly Asn Val Ser Asn Gly Gly Arg Ile Arg Cys Glu Glu Asn Asn
        115                 120                 125

cag aac caa tgc atc ccg tac aat tgc ctc agc aat ccc gaa gag gtg      432
Gln Asn Gln Cys Ile Pro Tyr Asn Cys Leu Ser Asn Pro Glu Glu Val
    130                 135                 140

ctc ctt gac gga gag agg atc tca acc ggg aac agt tcc atc gac atc      480
Leu Leu Asp Gly Glu Arg Ile Ser Thr Gly Asn Ser Ser Ile Asp Ile
145                 150                 155                 160

agc ttg agt ctc gtt cag ttc ctc gtg agc aac ttc gtg cct gga ggg      528
Ser Leu Ser Leu Val Gln Phe Leu Val Ser Asn Phe Val Pro Gly Gly
                165                 170                 175

gga ttt ctc gtg ggt ctc atc gac ttt gtg tgg ggt ata gtt gga ccg      576
Gly Phe Leu Val Gly Leu Ile Asp Phe Val Trp Gly Ile Val Gly Pro
            180                 185                 190

agt caa tgg gac gcc ttt ctc gtt cag atc gag cag ctc atc aac gag      624
Ser Gln Trp Asp Ala Phe Leu Val Gln Ile Glu Gln Leu Ile Asn Glu
        195                 200                 205

agg att gcc gag ttt gca agg aat gcc gca ata gca aac ctc gaa ggt      672
Arg Ile Ala Glu Phe Ala Arg Asn Ala Ala Ile Ala Asn Leu Glu Gly
    210                 215                 220

ctc ggc aac aac ttc aac atc tac gtc gaa gcg ttc aag gag tgg gag      720
Leu Gly Asn Asn Phe Asn Ile Tyr Val Glu Ala Phe Lys Glu Trp Glu
225                 230                 235                 240

gaa gac cct aac aac cca gag aca agg aca agg gtg atc gac agg ttc      768
Glu Asp Pro Asn Asn Pro Glu Thr Arg Thr Arg Val Ile Asp Arg Phe
                245                 250                 255

agg atc ctt gac gga ctt ctc gaa cgc gac att ccg agc ttc aga atc      816
Arg Ile Leu Asp Gly Leu Leu Glu Arg Asp Ile Pro Ser Phe Arg Ile
            260                 265                 270

agc gga ttc gaa gtc cct ttg ctc tct gtg tac gcc caa gct gcc aat      864
Ser Gly Phe Glu Val Pro Leu Leu Ser Val Tyr Ala Gln Ala Ala Asn
        275                 280                 285

ctc cac ctc gct atc ctc aga gac agc gtg atc ttc gga gaa aga tgg      912
Leu His Leu Ala Ile Leu Arg Asp Ser Val Ile Phe Gly Glu Arg Trp
    290                 295                 300

gga ctc act acc atc aac gtg aac gag aac tac aac agg ctc ata ag       959
Gly Leu Thr Thr Ile Asn Val Asn Glu Asn Tyr Asn Arg Leu Ile Arg
305                 310                 315                 320

gtccgccttg tttctcctct gtctcttgat ctgactaatc ttggtttatg attcgttgag   1019

taattttggg gaaagcttcg tccacagttt ttttttcgat gaacagtgcc gcagtggcgc   1079

tgatcttgta tgctatcctg caatcgtggt gaacttatgt cttttatatc cttcactacc   1139

atgaaaagac tagtaatctt tctcgatgta acatcgtcca gcactgctat taccgtgtgg   1199

tccatccgac agtctggctg aacacatcat acgatattga gcaaagatct atcttccctg   1259

ttctttaatg aaagacgtca ttttcatcag tatgatctaa gaatgttgca acttgcaagg   1319

aggcgtttct ttctttgaat ttaactaact cgttgagtgg ccctgtttct cggacgtaag   1379

gcctttgctg ctccacacat gtccattcga attttaccgt gtttagcaag ggcgaaaagt   1439

ttgcatcttg atgatttagc ttgactatgc gattgctttc ctggacccgt gcag g cac   1497
                                                            His

atc gac gag tac gcc gat cac tgt gcg aac acc tac aac cgg gga ctc      1545
Ile Asp Glu Tyr Ala Asp His Cys Ala Asn Thr Tyr Asn Arg Gly Leu
            325                 330                 335
```

-continued

```
aac aac ctt ccc aag tct acc tac caa gat tgg atc acc tac aac cgt      1593
Asn Asn Leu Pro Lys Ser Thr Tyr Gln Asp Trp Ile Thr Tyr Asn Arg
        340                 345                 350

ctc cgg aga gat ctt acc ctc act gtt ctc gat atc gca gct ttc ttc      1641
Leu Arg Arg Asp Leu Thr Leu Thr Val Leu Asp Ile Ala Ala Phe Phe
    355                 360                 365

ccc aac tac gac aac agg aga tac ccg ata caa ccc gtt gga caa ctc      1689
Pro Asn Tyr Asp Asn Arg Arg Tyr Pro Ile Gln Pro Val Gly Gln Leu
370                 375                 380                 385

acg aga gag gtg tac acc gat cca ctc atc aac ttc aac cct cag ctt      1737
Thr Arg Glu Val Tyr Thr Asp Pro Leu Ile Asn Phe Asn Pro Gln Leu
                390                 395                 400

caa agc gtg gca cag ctt cct acc ttc aac gtg atg gag tcc tca gcg      1785
Gln Ser Val Ala Gln Leu Pro Thr Phe Asn Val Met Glu Ser Ser Ala
            405                 410                 415

ata agg aac cct cat ctc ttc gac atc ctg aac aac ctc acc atc ttc      1833
Ile Arg Asn Pro His Leu Phe Asp Ile Leu Asn Asn Leu Thr Ile Phe
        420                 425                 430

acc gac tgg ttt agt gtg ggc agg aac ttc tac tgg gga ggc cac aga      1881
Thr Asp Trp Phe Ser Val Gly Arg Asn Phe Tyr Trp Gly Gly His Arg
    435                 440                 445

gtg atc agc tca ctc att ggc gga ggg aac atc acc tca ccc atc tat      1929
Val Ile Ser Ser Leu Ile Gly Gly Gly Asn Ile Thr Ser Pro Ile Tyr
450                 455                 460                 465

ggc aga gaa gcg aat caa gaa cct ccg agg agt ttc acc ttc aac gga      1977
Gly Arg Glu Ala Asn Gln Glu Pro Pro Arg Ser Phe Thr Phe Asn Gly
                470                 475                 480

ccg gtc ttc aga acc ttg agc aac cct aca ctc aga ctc ctc cag caa      2025
Pro Val Phe Arg Thr Leu Ser Asn Pro Thr Leu Arg Leu Leu Gln Gln
            485                 490                 495

cca tgg cca gca ccg cca ttc aac ctc aga ggc gtg gaa ggc gtg gag      2073
Pro Trp Pro Ala Pro Pro Phe Asn Leu Arg Gly Val Glu Gly Val Glu
        500                 505                 510

ttc tct acg cca acc aac tcc ttc acg tac aga gga aga gga acc gtc      2121
Phe Ser Thr Pro Thr Asn Ser Phe Thr Tyr Arg Gly Arg Gly Thr Val
    515                 520                 525

gat tct ctc aca gaa ctg cct cca gag gac aac tcc gtt cct ccg aga      2169
Asp Ser Leu Thr Glu Leu Pro Pro Glu Asp Asn Ser Val Pro Pro Arg
530                 535                 540                 545

gaa ggc tat agc cac aga ctt tgc cac gcc act ttc gtg cag aga agt      2217
Glu Gly Tyr Ser His Arg Leu Cys His Ala Thr Phe Val Gln Arg Ser
                550                 555                 560

ggc acg cca ttc ctc act aca ggc gtg gtg ttc agc tgg act cat agg      2265
Gly Thr Pro Phe Leu Thr Thr Gly Val Val Phe Ser Trp Thr His Arg
            565                 570                 575

agt gca aca ctc acc aac acg att gac cca gaa cgc atc aac cag ata      2313
Ser Ala Thr Leu Thr Asn Thr Ile Asp Pro Glu Arg Ile Asn Gln Ile
        580                 585                 590

cca ctc gtc aag gga ttc agg gtg tgg ggt ggg aca tca gtc atc act      2361
Pro Leu Val Lys Gly Phe Arg Val Trp Gly Gly Thr Ser Val Ile Thr
    595                 600                 605

gga cca ggc ttc acc ggc ggc gac att ctc cgt agg aac acc ttt ggc      2409
Gly Pro Gly Phe Thr Gly Gly Asp Ile Leu Arg Arg Asn Thr Phe Gly
610                 615                 620                 625

gac ttt gtg agc ctc caa gtc aac atc aac tct ccg att acc cag agg      2457
Asp Phe Val Ser Leu Gln Val Asn Ile Asn Ser Pro Ile Thr Gln Arg
                630                 635                 640

tat agg ctc agg ttc agg tat gcc tca tcg aga gat gcc aga gtg atc      2505
Tyr Arg Leu Arg Phe Arg Tyr Ala Ser Ser Arg Asp Ala Arg Val Ile
            645                 650                 655
```

-continued

```
gtg ctc aca ggg gct gcc agt act ggc gtg gga ggc cag gtg agt gtg     2553
Val Leu Thr Gly Ala Ala Ser Thr Gly Val Gly Gly Gln Val Ser Val
        660                 665                 670

aac atg cca ctc cag aag acc atg gag att ggc gag aac ctc act tca     2601
Asn Met Pro Leu Gln Lys Thr Met Glu Ile Gly Glu Asn Leu Thr Ser
    675                 680                 685

agg acc ttc cgc tat acg gac ttc tcc aac cca ttc agc ttc agg gca     2649
Arg Thr Phe Arg Tyr Thr Asp Phe Ser Asn Pro Phe Ser Phe Arg Ala
690                 695                 700                 705

aac cca gac atc atc ggc ata tca gag caa cca ctc ttt gga gct gga     2697
Asn Pro Asp Ile Ile Gly Ile Ser Glu Gln Pro Leu Phe Gly Ala Gly
                710                 715                 720

agc atc agt tca ggc gaa ctc tac atc gac aag atc gag atc atc ctt     2745
Ser Ile Ser Ser Gly Glu Leu Tyr Ile Asp Lys Ile Glu Ile Ile Leu
            725                 730                 735

gct gac gca act ttc gag gct gaa agc gac ctt gaa agg tga             2787
Ala Asp Ala Thr Phe Glu Ala Glu Ser Asp Leu Glu Arg
        740                 745                 750


<210> SEQ ID NO 6
<211> LENGTH: 750
<212> TYPE: PRT
<213> ORGANISM: Artificial Sequence
<220> FEATURE:
<223> OTHER INFORMATION: Synthetic Construct

<400> SEQUENCE: 6

Met Ala Ser Ile Ser Ser Ser Val Ala Thr Val Ser Arg Thr Ala Pro
1               5                   10                  15

Ala Gln Ala Asn Met Val Ala Pro Phe Thr Gly Leu Lys Ser Asn Ala
            20                  25                  30

Ala Phe Pro Thr Thr Lys Lys Ala Asn Asp Phe Ser Thr Leu Pro Ser
        35                  40                  45

Asn Gly Gly Arg Val Gln Cys Met Gln Val Trp Pro Ala Tyr Gly Asn
    50                  55                  60

Lys Lys Phe Glu Thr Leu Ser Tyr Leu Pro Pro Leu Ser Met Ala Pro
65                  70                  75                  80

Thr Val Met Met Ala Ser Ser Ala Thr Ala Val Ala Pro Phe Gln Gly
                85                  90                  95

Leu Lys Ser Thr Ala Ser Leu Pro Val Ala Arg Arg Ser Ser Arg Ser
            100                 105                 110

Leu Gly Asn Val Ser Asn Gly Gly Arg Ile Arg Cys Glu Glu Asn Asn
        115                 120                 125

Gln Asn Gln Cys Ile Pro Tyr Asn Cys Leu Ser Asn Pro Glu Glu Val
    130                 135                 140

Leu Leu Asp Gly Glu Arg Ile Ser Thr Gly Asn Ser Ser Ile Asp Ile
145                 150                 155                 160

Ser Leu Ser Leu Val Gln Phe Leu Val Ser Asn Phe Val Pro Gly Gly
                165                 170                 175

Gly Phe Leu Val Gly Leu Ile Asp Phe Val Trp Gly Ile Val Gly Pro
            180                 185                 190

Ser Gln Trp Asp Ala Phe Leu Val Gln Ile Glu Gln Leu Ile Asn Glu
        195                 200                 205

Arg Ile Ala Glu Phe Ala Arg Asn Ala Ala Ile Ala Asn Leu Glu Gly
    210                 215                 220

Leu Gly Asn Asn Phe Asn Ile Tyr Val Glu Ala Phe Lys Glu Trp Glu
225                 230                 235                 240
```

```
Glu Asp Pro Asn Asn Pro Glu Thr Arg Thr Arg Val Ile Asp Arg Phe
                245                 250                 255

Arg Ile Leu Asp Gly Leu Leu Glu Arg Asp Ile Pro Ser Phe Arg Ile
            260                 265                 270

Ser Gly Phe Glu Val Pro Leu Leu Ser Val Tyr Ala Gln Ala Ala Asn
        275                 280                 285

Leu His Leu Ala Ile Leu Arg Asp Ser Val Ile Phe Gly Glu Arg Trp
    290                 295                 300

Gly Leu Thr Thr Ile Asn Val Asn Glu Asn Tyr Asn Arg Leu Ile Arg
305                 310                 315                 320

His Ile Asp Glu Tyr Ala Asp His Cys Ala Asn Thr Tyr Asn Arg Gly
                325                 330                 335

Leu Asn Asn Leu Pro Lys Ser Thr Tyr Gln Asp Trp Ile Thr Tyr Asn
            340                 345                 350

Arg Leu Arg Arg Asp Leu Thr Leu Thr Val Leu Asp Ile Ala Ala Phe
        355                 360                 365

Phe Pro Asn Tyr Asp Asn Arg Arg Tyr Pro Ile Gln Pro Val Gly Gln
    370                 375                 380

Leu Thr Arg Glu Val Tyr Thr Asp Pro Leu Ile Asn Phe Asn Pro Gln
385                 390                 395                 400

Leu Gln Ser Val Ala Gln Leu Pro Thr Phe Asn Val Met Glu Ser Ser
                405                 410                 415

Ala Ile Arg Asn Pro His Leu Phe Asp Ile Leu Asn Asn Leu Thr Ile
            420                 425                 430

Phe Thr Asp Trp Phe Ser Val Gly Arg Asn Phe Tyr Trp Gly Gly His
        435                 440                 445

Arg Val Ile Ser Ser Leu Ile Gly Gly Gly Asn Ile Thr Ser Pro Ile
    450                 455                 460

Tyr Gly Arg Glu Ala Asn Gln Glu Pro Pro Arg Ser Phe Thr Phe Asn
465                 470                 475                 480

Gly Pro Val Phe Arg Thr Leu Ser Asn Pro Thr Leu Arg Leu Leu Gln
                485                 490                 495

Gln Pro Trp Pro Ala Pro Pro Phe Asn Leu Arg Gly Val Glu Gly Val
            500                 505                 510

Glu Phe Ser Thr Pro Thr Asn Ser Phe Thr Tyr Arg Gly Arg Gly Thr
        515                 520                 525

Val Asp Ser Leu Thr Glu Leu Pro Pro Glu Asp Asn Ser Val Pro Pro
    530                 535                 540

Arg Glu Gly Tyr Ser His Arg Leu Cys His Ala Thr Phe Val Gln Arg
545                 550                 555                 560

Ser Gly Thr Pro Phe Leu Thr Thr Gly Val Val Phe Ser Trp Thr His
                565                 570                 575

Arg Ser Ala Thr Leu Thr Asn Thr Ile Asp Pro Glu Arg Ile Asn Gln
            580                 585                 590

Ile Pro Leu Val Lys Gly Phe Arg Val Trp Gly Gly Thr Ser Val Ile
        595                 600                 605

Thr Gly Pro Gly Phe Thr Gly Gly Asp Ile Leu Arg Arg Asn Thr Phe
    610                 615                 620

Gly Asp Phe Val Ser Leu Gln Val Asn Ile Asn Ser Pro Ile Thr Gln
625                 630                 635                 640

Arg Tyr Arg Leu Arg Phe Arg Tyr Ala Ser Ser Arg Asp Ala Arg Val
                645                 650                 655
```

-continued

```
Ile Val Leu Thr Gly Ala Ala Ser Thr Gly Val Gly Gly Gln Val Ser
            660                 665                 670

Val Asn Met Pro Leu Gln Lys Thr Met Glu Ile Gly Glu Asn Leu Thr
        675                 680                 685

Ser Arg Thr Phe Arg Tyr Thr Asp Phe Ser Asn Pro Phe Ser Phe Arg
    690                 695                 700

Ala Asn Pro Asp Ile Ile Gly Ile Ser Glu Gln Pro Leu Phe Gly Ala
705                 710                 715                 720

Gly Ser Ile Ser Ser Gly Glu Leu Tyr Ile Asp Lys Ile Glu Ile Ile
                725                 730                 735

Leu Ala Asp Ala Thr Phe Glu Ala Glu Ser Asp Leu Glu Arg
            740                 745                 750


<210> SEQ ID NO 7
<211> LENGTH: 20
<212> TYPE: DNA
<213> ORGANISM: Artificial Sequence
<220> FEATURE:
<223> OTHER INFORMATION: synthetic primer

<400> SEQUENCE: 7

gagcaacttc gtgcctggag                                                   20


<210> SEQ ID NO 8
<211> LENGTH: 20
<212> TYPE: DNA
<213> ORGANISM: Artificial Sequence
<220> FEATURE:
<223> OTHER INFORMATION: synthetic primer

<400> SEQUENCE: 8

ggtggagatt ggcagcttgg                                                   20


<210> SEQ ID NO 9
<211> LENGTH: 2023
<212> TYPE: DNA
<213> ORGANISM: Zea mays

<400> SEQUENCE: 9

ctgcagtgca gcgtgacccg gtcgtgcccc tctctagaga taatgagcat tgcatgtcta      60

agttataaaa aattaccaca tatttttttt gtcacacttg tttgaagtgc agtttatcta     120

tctttataca tatatttaaa ctttactcta cgaataatat aatctatagt actacaataa     180

tatcagtgtt ttagagaatc atataaatga acagttagac atggtctaaa ggacaattga     240

gtattttgac aacaggactc tacagtttta tctttttagt gtgcatgtgt tctccttttt     300

ttttgcaaat agcttcacct atataatact tcatccattt tattagtaca tccatttagg     360

gtttagggtt aatggttttt atagactaat ttttttagta catctatttt attctatttt     420

agcctctaaa ttaagaaaac taaaactcta ttttagtttt tttatttaat aatttagata     480

taaaatagaa taaaataaag tgactaaaaa ttaaacaaat accctttaag aaattaaaaa     540

aactaaggaa acatttttct tgtttcgagt agataatgcc agcctgttaa acgccgtcga     600

tcgacgagtc taacggacac caaccagcga accagcagcg tcgcgtcggg ccaagcgaag     660

cagacggcac ggcatctctg tcgctgcctc tggacccctc tcgagagttc cgctccaccg     720

ttggacttgc tccgctgtcg gcatccagaa attgcgtggc ggagcggcag acgtgagccg     780

gcacggcagg cggcctcctc ctcctctcac ggcaccggca gctacggggg attcctttcc     840

caccgctcct tcgctttccc ttcctcgccc gccgtaataa atagacaccc cctccacacc     900
```

```
ctctttcccc aacctcgtgt tgttcggagc gcacacacac acaaccagat ctcccccaaa    960
tccacccgtc ggcacctccg cttcaaggta cgccgctcgt cctccccccc cccccctctc   1020
taccttctct agatcggcgt tccggtccat gcttagggcc cggtagttct acttctgtcc   1080
atgtttgtgt tagatccgtg tttgtgttag atccgtgcta ctagcgttcg tacacggatg   1140
cgacctgtac gtcagacacg ttctgattgc taacttgcca gtgtttctct ttggggaatc   1200
ctgggatggc tctagccgtt ccgcagacgg gatcgatttc atgatttttt ttgtttcgtt   1260
gcatagggtt tggtttgccc ttttccttta tttcaatata tgccgtgcac ttgtttgtcg   1320
ggtcatcttt tcatgctttt ttttgtcttg gttgtgatga tgtggtctgg ttgggcggtc   1380
gttctagatc ggagtagaat tctgtttcaa actacctggt ggatttatta attttggatc   1440
tgtatgtgtg tgccatacat attcatagtt acgaattgaa gatgatggat ggaaatatcg   1500
atctaggata ggtatacatg ttgatgcggg ttttactgat gcatatacag agatgctttt   1560
tgttcgcttg gttgtgatga tgtggtgtgg ttgggcggtc gttcattcgt tctagatcgg   1620
agtagaatac tgtttcaaac tacctggtgt atttattaat tttggaactg tatgtgtgtg   1680
tcatacatct tcatagttac gagtttaaga tggatggaaa tatcgatcta ggataggtat   1740
acatgttgat gtgggtttta ctgatgcata tacatgatgg catatgcagc atctattcat   1800
atgctctaac cttgagtacc tatctattat aataaacaag tatgttttat aattattttg   1860
atcttgatat acttggatga tggcatatgc agcagctata tgtggatttt tttagccctg   1920
ccttcatacg ctatttattt gcttggtact gtttcttttg tcgatgctca ccctgttgtt   1980
tggtgttact tctgcaggtc gaccgccggg gatcaccaaa acc                     2023
```

<210> SEQ ID NO 10
<211> LENGTH: 2056
<212> TYPE: DNA
<213> ORGANISM: Zea mays

<400> SEQUENCE: 10

```
actcaaacct catgttttac ccttttactc aaagttgcac tttgtaccct ccatttcaac     60
tcttttggac ttagtgcctt taaattgcct tcaagtgaac ctatgattat actcatatca    120
aactagttag tcaacgttgg tgcgttgaac acttaatcac caaaacaggt agaaatgtat    180
atcttgcgca tttccctttc agaacatttt ggaaacgctg ccaatactgc ttcttattcc    240
attaacccca actggtatgt caacagtggc accaatgacc ttcttactag cgatcttgat    300
cacctaagtg tccacgagcg ctacaccggc aaggactcca tttaggtcac cagttgcaca    360
ggtctgccaa tttcttatac tggtcattcg ttgcttcctg gcttgactcg tcctctttac    420
ctactcaata ttttacatgt gcctggtaca tgtctgccta ttacatgtct gactcgtttg    480
cttatttggg ctaggggcac cataatttta taccttttaa catattgatc aagcagccat    540
gaccgaagaa gatgcaatca caaatagcct ttatgaatta gagttctaaa tggactattt    600
ggttgaaaaa gttggagact tgcatgggct agagttctta tttcgggaac agggtgagtt    660
gtgaaatcta ttgcttctcg aaagacacta gtagtacaag tgcttttggt tcatgacctc    720
caccaaaagg agggggcatg tgttgaacaa caaatttggc acttggatag tcggatggtc    780
cggccttgtg gcccgaacgg tctatgccct ggacgattcg caggagtagt tcggaaggta    840
cgcgattaga ttagttcagg ctggagtcct tatcccatgc gtggttatcc taacaaactc    900
ggacggaact attggatctc gcctaggaat gggtccaaac ccccctatat acatgatagg    960
```

-continued

```
tacgaccaaa tgagaataca agatcaaatc gaaaccaatt tattacatta tttatcttca   1020

tgccttagga gtagatgtag tgtagctcta gttgtagttt cccaaactca accttgacct   1080

ctttagctct acgtcatcta gaggtgcttt aggtggcttg ttgatatcaa aacaacccta   1140

tgatctcttc tccccgacgg ggtcctcgag agacgatatt taggttctac acaaaaccct   1200

ctacggcatc gtggatggtc caccacctac aagtggacgg tccacgcgcc tgcagagaag   1260

agcatagtta tttgctccat ggtgacctac acgcgaacgg tccagtgacc tatcacgaac   1320

cgttcagcac cttgcagaga ggtctccaag gtctcgacta ctcatgagcg gaatctagtg   1380

attattggtg tttagcgcaa aaacggcgcc aacagtaggg tttacgtgcg aagtaagatg   1440

gagggtcata gagtttaaga tatagaaatt gacagattcc tcctattgtt ggataactcg   1500

gcggattttg ttcagattga tttagaccat tttcacacac tatcagatgc cgatcctagc   1560

taatggccag aatctgagaa acaaacaccc cgaaacgtac agcggtgggc gaggtggtta   1620

ggtcactgtt caccgagttt tgataagttt ctgtccgcgt cagcgccagc tacgcgcgct   1680

ggaaaatgct gactattttg gctgcaagca tgggataacc atggattttt tttcctgcag   1740

tgttgctatc tgttctttgt ttcgtagtgg ctgtttatcc tcgtgtgcct cgcgtgcgta   1800

tatacacaca cgtcctgcct gcacgcaacg cagctctata aatacctcat caccggtgca   1860

ctcgcttaat atatatccaa caaccagcag tgcaacaagc aagatttacc tgcccgtgag   1920

tgtgcctttc aataaatataa tgtcttattt tattattatg tttttgcagt gatagtagtc   1980

tgtaataaat ctctcctttc aatatatata attcacatgc cagatcgatc atatcgtcaa   2040

ctcgtccggc agttcg                                                   2056
```

```
<210> SEQ ID NO 11
<211> LENGTH: 1854
<212> TYPE: DNA
<213> ORGANISM: Artificial Sequence
<220> FEATURE:
<223> OTHER INFORMATION: synthetic sequence
<220> FEATURE:
<221> NAME/KEY: CDS
<222> LOCATION: (1)..(1851)

<400> SEQUENCE: 11

atg gct gac aac aac ccc aac atc aac gag tgc atc ccc tac aac tgc      48
Met Ala Asp Asn Asn Pro Asn Ile Asn Glu Cys Ile Pro Tyr Asn Cys
1               5                   10                  15

ctg agc aac cca gag gtg gag gtg ctg ggt ggt gag agg atc gag acc      96
Leu Ser Asn Pro Glu Val Glu Val Leu Gly Gly Glu Arg Ile Glu Thr
            20                  25                  30

ggt tac acc ccc atc gac atc agc ctg agc ctg acc cag ttc ctg ctg     144
Gly Tyr Thr Pro Ile Asp Ile Ser Leu Ser Leu Thr Gln Phe Leu Leu
        35                  40                  45

agc gag ttc gtg cct ggt gct ggc ttc gtg ctg gga cta gtg gac atc     192
Ser Glu Phe Val Pro Gly Ala Gly Phe Val Leu Gly Leu Val Asp Ile
    50                  55                  60

atc tgg ggc atc ttc ggt ccc agc cag tgg gat gcc ttc ctg gtg cag     240
Ile Trp Gly Ile Phe Gly Pro Ser Gln Trp Asp Ala Phe Leu Val Gln
65                  70                  75                  80

atc gaa cag tta att aac caa aga ata gaa gaa ttc gct agg aac caa     288
Ile Glu Gln Leu Ile Asn Gln Arg Ile Glu Glu Phe Ala Arg Asn Gln
                85                  90                  95

gcc atc tct aga ctg gag ggc ctg agc aac ctg tac cag atc tac gcc     336
Ala Ile Ser Arg Leu Glu Gly Leu Ser Asn Leu Tyr Gln Ile Tyr Ala
            100                 105                 110
```

-continued

```
gag agc ttc cgc gag tgg gag gct gac ccc acc aac cca gcc ctg cgc      384
Glu Ser Phe Arg Glu Trp Glu Ala Asp Pro Thr Asn Pro Ala Leu Arg
        115                 120                 125

gag gag atg cgc atc cag ttc aac gac atg aac tct gcc ctg acc acc      432
Glu Glu Met Arg Ile Gln Phe Asn Asp Met Asn Ser Ala Leu Thr Thr
    130                 135                 140

gcc atc cca ctc ttc gct gtc cag aac tac cag gtc cct ctc ctg tct      480
Ala Ile Pro Leu Phe Ala Val Gln Asn Tyr Gln Val Pro Leu Leu Ser
145                 150                 155                 160

gtc tat gtg caa gct gcc aac ctc cat ctc agc gtc ctt cgc gac gtg      528
Val Tyr Val Gln Ala Ala Asn Leu His Leu Ser Val Leu Arg Asp Val
                165                 170                 175

agc gtc ttt ggg cag agg tgg ggg ttc gac gct gcc acc atc aac agc      576
Ser Val Phe Gly Gln Arg Trp Gly Phe Asp Ala Ala Thr Ile Asn Ser
            180                 185                 190

cgc tac aac gac ctg acg cgt ctg atc ggc aac tac acc gac cac gca      624
Arg Tyr Asn Asp Leu Thr Arg Leu Ile Gly Asn Tyr Thr Asp His Ala
        195                 200                 205

gtg aga tgg tac aac act ggg ctt gag agg gtc tgg ggt ccc gac agc      672
Val Arg Trp Tyr Asn Thr Gly Leu Glu Arg Val Trp Gly Pro Asp Ser
    210                 215                 220

cgc gac tgg atc agg tac aac cag ttc agg cgt gaa ctc act ctc acc      720
Arg Asp Trp Ile Arg Tyr Asn Gln Phe Arg Arg Glu Leu Thr Leu Thr
225                 230                 235                 240

gtc ttg gat atc gtc agt ctc ttc ccc aac tac gac agc agg acc tac      768
Val Leu Asp Ile Val Ser Leu Phe Pro Asn Tyr Asp Ser Arg Thr Tyr
                245                 250                 255

cct atc cgg act gtg agc cag ctg acc cgc gag atc tac acc aac ccc      816
Pro Ile Arg Thr Val Ser Gln Leu Thr Arg Glu Ile Tyr Thr Asn Pro
            260                 265                 270

gtg ctg gag aac ttc gac ggc agc ttc agg ggc tct gcc cag ggc atc      864
Val Leu Glu Asn Phe Asp Gly Ser Phe Arg Gly Ser Ala Gln Gly Ile
        275                 280                 285

gag ggc agc atc cgc agc ccc cac ctg atg gac atc ctg aac agc atc      912
Glu Gly Ser Ile Arg Ser Pro His Leu Met Asp Ile Leu Asn Ser Ile
    290                 295                 300

acc atc tac act gac gcc cac agg ggt gag tac tac tgg tct ggc cac      960
Thr Ile Tyr Thr Asp Ala His Arg Gly Glu Tyr Tyr Trp Ser Gly His
305                 310                 315                 320

cag atc atg gct tct ccc gtg ggc ttc agc ggt ccc gag ttc acc ttc     1008
Gln Ile Met Ala Ser Pro Val Gly Phe Ser Gly Pro Glu Phe Thr Phe
                325                 330                 335

ccc ctg tac ggc aca atg ggc aac gct gcc cca cag cag agg atc gtg     1056
Pro Leu Tyr Gly Thr Met Gly Asn Ala Ala Pro Gln Gln Arg Ile Val
            340                 345                 350

gcc cag ctg ggc cag ggc gtg tac cgc acc ctg agc agc acc ctg tac     1104
Ala Gln Leu Gly Gln Gly Val Tyr Arg Thr Leu Ser Ser Thr Leu Tyr
        355                 360                 365

agg agg ccc ttc aac atc ggc atc aac aac cag cag ctg agc gtg ctg     1152
Arg Arg Pro Phe Asn Ile Gly Ile Asn Asn Gln Gln Leu Ser Val Leu
    370                 375                 380

gat ggc acc gag ttc gcc tac ggc acc agc agc aac ctg ccc agc gcc     1200
Asp Gly Thr Glu Phe Ala Tyr Gly Thr Ser Ser Asn Leu Pro Ser Ala
385                 390                 395                 400

gta tac cgc aag agc ggc act gtg gac agc ctg gac gag atc cca ccc     1248
Val Tyr Arg Lys Ser Gly Thr Val Asp Ser Leu Asp Glu Ile Pro Pro
                405                 410                 415

cag aac aac aac gtg ccc cct agg cag ggg ttc tct cat cgc ctc tca     1296
Gln Asn Asn Asn Val Pro Pro Arg Gln Gly Phe Ser His Arg Leu Ser
            420                 425                 430
```

```
cac gtg agc atg ttc cgc agc ggc ttc agc aac agc agc gtg agc atc     1344
His Val Ser Met Phe Arg Ser Gly Phe Ser Asn Ser Ser Val Ser Ile
        435                 440                 445

atc agg gct ccc atg ttc agc tgg atc cac cgc agc gct gag ttc aac     1392
Ile Arg Ala Pro Met Phe Ser Trp Ile His Arg Ser Ala Glu Phe Asn
    450                 455                 460

aac atc att cca agt agc cag atc act cag atc cca ctc acc aag agc     1440
Asn Ile Ile Pro Ser Ser Gln Ile Thr Gln Ile Pro Leu Thr Lys Ser
465                 470                 475                 480

acc aac ctg ggc tcc ggg act agc gtt gtc aag gga cca ggg ttc act     1488
Thr Asn Leu Gly Ser Gly Thr Ser Val Val Lys Gly Pro Gly Phe Thr
                485                 490                 495

gga ggc gac atc ctg agg agg acc agc cca ggc cag atc agc acc tta     1536
Gly Gly Asp Ile Leu Arg Arg Thr Ser Pro Gly Gln Ile Ser Thr Leu
            500                 505                 510

agg gtg aac atc acc gct ccc ctc agc caa cgc tac agg gtc agg atc     1584
Arg Val Asn Ile Thr Ala Pro Leu Ser Gln Arg Tyr Arg Val Arg Ile
        515                 520                 525

agg tac gct tcc acc acc aac ctg cag ttc cac acc agc atc gac ggc     1632
Arg Tyr Ala Ser Thr Thr Asn Leu Gln Phe His Thr Ser Ile Asp Gly
    530                 535                 540

agg ccc atc aac cag ggc aac ttc agc gcc acc atg agc agc ggc agc     1680
Arg Pro Ile Asn Gln Gly Asn Phe Ser Ala Thr Met Ser Ser Gly Ser
545                 550                 555                 560

aac ctg cag agc gga agc ttc cgc act gtg ggc ttc act acc cca ttc     1728
Asn Leu Gln Ser Gly Ser Phe Arg Thr Val Gly Phe Thr Thr Pro Phe
                565                 570                 575

aac ttc tcc aac ggc agc agc gtg ttc acc ctg tct gcc cac gtg ttc     1776
Asn Phe Ser Asn Gly Ser Ser Val Phe Thr Leu Ser Ala His Val Phe
            580                 585                 590

aac agc ggc aac gag gtg tac atc gac agg atc gag ttt gtc cca gct     1824
Asn Ser Gly Asn Glu Val Tyr Ile Asp Arg Ile Glu Phe Val Pro Ala
        595                 600                 605

gag gtg acc ttc gaa gct gag tac gac tga                             1854
Glu Val Thr Phe Glu Ala Glu Tyr Asp
    610                 615
```

<210> SEQ ID NO 12
<211> LENGTH: 617
<212> TYPE: PRT
<213> ORGANISM: Artificial Sequence
<220> FEATURE:
<223> OTHER INFORMATION: Synthetic Construct

<400> SEQUENCE: 12

```
Met Ala Asp Asn Asn Pro Asn Ile Asn Glu Cys Ile Pro Tyr Asn Cys
1               5                   10                  15

Leu Ser Asn Pro Glu Val Glu Val Leu Gly Gly Glu Arg Ile Glu Thr
            20                  25                  30

Gly Tyr Thr Pro Ile Asp Ile Ser Leu Ser Leu Thr Gln Phe Leu Leu
        35                  40                  45

Ser Glu Phe Val Pro Gly Ala Gly Phe Val Leu Gly Leu Val Asp Ile
    50                  55                  60

Ile Trp Gly Ile Phe Gly Pro Ser Gln Trp Asp Ala Phe Leu Val Gln
65                  70                  75                  80

Ile Glu Gln Leu Ile Asn Gln Arg Ile Glu Glu Phe Ala Arg Asn Gln
                85                  90                  95

Ala Ile Ser Arg Leu Glu Gly Leu Ser Asn Leu Tyr Gln Ile Tyr Ala
            100                 105                 110
```

```
Glu Ser Phe Arg Glu Trp Glu Ala Asp Pro Thr Asn Pro Ala Leu Arg
        115                 120                 125

Glu Glu Met Arg Ile Gln Phe Asn Asp Met Asn Ser Ala Leu Thr Thr
    130                 135                 140

Ala Ile Pro Leu Phe Ala Val Gln Asn Tyr Gln Val Pro Leu Leu Ser
145                 150                 155                 160

Val Tyr Val Gln Ala Ala Asn Leu His Leu Ser Val Leu Arg Asp Val
                165                 170                 175

Ser Val Phe Gly Gln Arg Trp Gly Phe Asp Ala Ala Thr Ile Asn Ser
            180                 185                 190

Arg Tyr Asn Asp Leu Thr Arg Leu Ile Gly Asn Tyr Thr Asp His Ala
        195                 200                 205

Val Arg Trp Tyr Asn Thr Gly Leu Glu Arg Val Trp Gly Pro Asp Ser
    210                 215                 220

Arg Asp Trp Ile Arg Tyr Asn Gln Phe Arg Arg Glu Leu Thr Leu Thr
225                 230                 235                 240

Val Leu Asp Ile Val Ser Leu Phe Pro Asn Tyr Asp Ser Arg Thr Tyr
                245                 250                 255

Pro Ile Arg Thr Val Ser Gln Leu Thr Arg Glu Ile Tyr Thr Asn Pro
            260                 265                 270

Val Leu Glu Asn Phe Asp Gly Ser Phe Arg Gly Ser Ala Gln Gly Ile
        275                 280                 285

Glu Gly Ser Ile Arg Ser Pro His Leu Met Asp Ile Leu Asn Ser Ile
    290                 295                 300

Thr Ile Tyr Thr Asp Ala His Arg Gly Glu Tyr Tyr Trp Ser Gly His
305                 310                 315                 320

Gln Ile Met Ala Ser Pro Val Gly Phe Ser Gly Pro Glu Phe Thr Phe
                325                 330                 335

Pro Leu Tyr Gly Thr Met Gly Asn Ala Ala Pro Gln Gln Arg Ile Val
            340                 345                 350

Ala Gln Leu Gly Gln Gly Val Tyr Arg Thr Leu Ser Ser Thr Leu Tyr
        355                 360                 365

Arg Arg Pro Phe Asn Ile Gly Ile Asn Asn Gln Gln Leu Ser Val Leu
    370                 375                 380

Asp Gly Thr Glu Phe Ala Tyr Gly Thr Ser Ser Asn Leu Pro Ser Ala
385                 390                 395                 400

Val Tyr Arg Lys Ser Gly Thr Val Asp Ser Leu Asp Glu Ile Pro Pro
                405                 410                 415

Gln Asn Asn Asn Val Pro Pro Arg Gln Gly Phe Ser His Arg Leu Ser
            420                 425                 430

His Val Ser Met Phe Arg Ser Gly Phe Ser Asn Ser Ser Val Ser Ile
        435                 440                 445

Ile Arg Ala Pro Met Phe Ser Trp Ile His Arg Ser Ala Glu Phe Asn
    450                 455                 460

Asn Ile Ile Pro Ser Ser Gln Ile Thr Gln Ile Pro Leu Thr Lys Ser
465                 470                 475                 480

Thr Asn Leu Gly Ser Gly Thr Ser Val Val Lys Gly Pro Gly Phe Thr
                485                 490                 495

Gly Gly Asp Ile Leu Arg Arg Thr Ser Pro Gly Gln Ile Ser Thr Leu
            500                 505                 510

Arg Val Asn Ile Thr Ala Pro Leu Ser Gln Arg Tyr Arg Val Arg Ile
        515                 520                 525
```

-continued

```
Arg Tyr Ala Ser Thr Thr Asn Leu Gln Phe His Thr Ser Ile Asp Gly
    530                 535                 540

Arg Pro Ile Asn Gln Gly Asn Phe Ser Ala Thr Met Ser Ser Gly Ser
545                 550                 555                 560

Asn Leu Gln Ser Gly Ser Phe Arg Thr Val Gly Phe Thr Thr Pro Phe
                565                 570                 575

Asn Phe Ser Asn Gly Ser Ser Val Phe Thr Leu Ser Ala His Val Phe
            580                 585                 590

Asn Ser Gly Asn Glu Val Tyr Ile Asp Arg Ile Glu Phe Val Pro Ala
        595                 600                 605

Glu Val Thr Phe Glu Ala Glu Tyr Asp
    610                 615


<210> SEQ ID NO 13
<211> LENGTH: 2145
<212> TYPE: DNA
<213> ORGANISM: Oryza sativa

<400> SEQUENCE: 13

cctcagccgc ctttcactat ctttttgcc cgagtcattg tcatgtgaac cttggcatgt      60

ataatcggtg aattgcgtcg attttcctct tataggtggg ccaatgaatc cgtgtgatcg    120

cgtctgattg gctagagata tgtttcttcc ttgttggatg tattttcata cataatcata    180

tgcatacaaa tatttcatta cactttatag aaatggtcag taataaaccc tatcactatg    240

tctggtgttt cattttattt gcttttaaac gaaaattgac ttcctgattc aatatttaag    300

gatcgtcaac ggtgtgcagt tactaaattc tggtttgtag gaactatagt aaactattca    360

agtcttcact tattgtgcac tcacctctcg ccacatcacc acagatgtta ttcacgtctt    420

aaatttgaac tacacatcat attgacacaa tatttttttt aaataagcga ttaaaaccta    480

gcctctatgt caacaatggt gtacataacc agcgaagttt agggagtaaa aaacatcgcc    540

ttacacaaag ttcgctttaa aaaataaaga gtaaatttta ctttggacca cccttcaacc    600

aatgtttcac tttagaacga gtaattttat tattgtcact ttggaccacc ctcaaatctt    660

ttttccatct acatccaatt tatcatgtca aagaaatggt ctacatacag ctaaggagat    720

ttatcgacga atagtagcta gcatactcga ggtcattcat atgcttgaga agagagtcgg    780

gatagtccaa aataaaacaa aggtaagatt acctggtcaa aagtgaaaac atcagttaaa    840

aggtggtata aagtaaaata tcggtaataa aaggtggccc aaagtgaaat ttactctttt    900

ctactattat aaaaattgag gatgtttttg tcggtacttt gatacgtcat ttttgtatga    960

attggttttt aagtttattc gcttttggaa atgcatatct gtatttgagt cgggttttaa   1020

gttcgtttgc ttttgtaaat acagagggat ttgtataaga aatatcttta aaaaaaccca   1080

tatgctaatt tgacataatt tttgagaaaa atatatattc aggcgaattc tcacaatgaa   1140

caataataag attaaaatag ctttccccccg ttgcagcgca tgggtatttt ttctagtaaa   1200

aataaaagat aaacttagac tcaaaacatt tacaaaaaca acccctaaag ttcctaaagc   1260

ccaaagtgct atccacgatc catagcaagc ccagcccaac ccaacccaac ccaacccacc   1320

ccagtccagc caactggaca atagtctcca caccccccca ctatcaccgt gagttgtccg   1380

cacgcaccgc acgtctcgca gccaaaaaaa aaaaaagaaa gaaaaaaaag aaaaagaaaa   1440

aacagcaggt gggtccgggt cgtgggggcc ggaaacgcga ggaggatcgc gagccagcga   1500

cgaggccggc cctccctccg cttccaaaga aacgcccccc atcgccacta tatacatacc   1560

ccccccctctc ctcccatccc cccaacccta ccaccaccac caccaccacc tccacctcct   1620
```

-continued

```
cccccctcgc tgccggacga cgagctcctc ccccctcccc ctccgccgcc gccgcgccgg   1680

taaccacccc gcccctctcc tctttctttc tccgtttttt ttttccgtct cggtctcgat   1740

ctttggcctt ggtagtttgg gtgggcgaga ggcggcttcg tgcgcgccca gatcggtgcg   1800

cgggaggggc gggatctcgc ggctggggct ctcgccggcg tggatccggc ccggatctcg   1860

cggggaatgg ggctctcgga tgtagatctg cgatccgccg ttgttggggg agatgatggg   1920

gggtttaaaa tttccgccat gctaaacaag atcaggaaga ggggaaaagg gcactatggt   1980

ttatattttt atatatttct gctgcttcgt caggcttaga tgtgctagat ctttctttct   2040

tctttttgtg ggtagaattt gaatccctca gcattgttca tcggtagttt ttcttttcat   2100

gatttgtgac aaatgcagcc tcgtgcggag ctttttgta ggtag                  2145


<210> SEQ ID NO 14
<211> LENGTH: 889
<212> TYPE: DNA
<213> ORGANISM: Zea mays

<400> SEQUENCE: 14

gagacgaata tttaggtttt acacaaaacc cttttacggc atcgtggatg gtccaccacc     60

tacaagtgga cggtccacgc gcctgcagag aagagcatag ttatttgctc catggtgacc    120

tacacgcgaa cggtccagtg acctatcacg aaccgttcag caccttgcag agaggtctcc    180

aaggtctcga ctactcatga gcggaatcta gtgattattg gtgtttagcg caaaaacggc    240

gccaacagta gggtttacgt gcgaagtaag atggagggtc atagagttta agatatagaa    300

attgacagat tcctcctatt gttggataac tcggcggatt ttgttcagat tgatttagac    360

cattttcaca cactatcaga tgccgatcct agctaatggc cagaatctga gaaacaaaca    420

ccccgaaacg tacagcggtg ggcgaggtgg ttaggtcact gttcaccgag ttttgataag    480

tttctgtccg cgtcagcgcc agctacgcgc gctggaaaat gctgactatt ttggctgcaa    540

gcatgggata accatggatt ttttttcctg cagtgttgct atctgttctt tgtttcgtag    600

tggctgttta tcctcgtgtg cctggcgtgc gtatatacac acacgtcctg cctgcacgca    660

acgcagctct ataaatacct catcaccggt gcactcgctt aatatatatc caacaaccag    720

cagtgcaaca agcaagattt acctgcccgt gagtgtgcct ttcaataata taatgtctta    780

ttttattatt atgtttttgc agtgatagta gtctgtaata aatctctcct ttcaatatat    840

ataattcaca tgccagatcg atcatatcgt caactggtcc ggcagttcg               889
```

GENES ENCODING INSECTICIDAL PROTEINS

CROSS-REFERENCE TO RELATED APPLICATIONS

This application is the U.S. National Stage filing of International Application No. PCT/EP2008/004550, filed May 28, 2008, which claims priority to EP 070 108 72.5, filed Jun. 1, 2007, and U.S. Provisional Patent Application No. 60/934,367, filed Jun. 13, 2007, the disclosures of each of which are hereby incorporated by reference.

The present invention relates to new DNA sequences encoding insecticidal proteins produced by *Bacillus thuringiensis* strains. Particularly, new chimeric genes encoding a Cry1C protein are provided which are useful to protect plants from insect damage. Also included herein are plant cells or plants, particularly rice plant cells or plants, comprising such genes and methods of making or using them, as well as plant cells or plants comprising a cry1C chimeric gene and at least one other gene encoding an insecticidal protein, such as a chimeric gene encoding a Cry1A protein.

BACKGROUND OF THE INVENTION

Strains and proteins derived from *Bacillus thuringiensis* (abbreviated herein as "Bt") are well known for their specific toxicity to insect pests, and they have been used since almost a century to control insect pests. Some transgenic plant species expressing Bt proteins are now available, and they successfully limit insect damage on plants.

Despite the isolation of quite a number of insecticidal Bt proteins, only a few Bt proteins have been expressed in transgenic plants that have been commercialized, and this only in some crops.

Insect pests are important constraints for rice production and occur in all rice growing environments. Insects reduce rice yields substantially and losses due to insects in Asia (excluding China) have been reported to be about 31.5% (Heinrichs, 1994). Insect resistance in rice has been reported by expressing genes encoding insecticidal Cry1Ab or Cry1Ac proteins of *Bacillus thuringiensis* (e.g., Fujimoto et al., 1993; Wunn et al., 1996; Wu et al. 1997; Ghareyazie et al., 1997; Nayak et al., 1997; and Cheng et al., 1998) in rice plants. Toxicity of isolated *Bacillus thuringiensis* crystal proteins to some Lepidopteran rice insect pests has been evaluated for some proteins of the classes of Bt proteins Cry1Aa, Cry1Ab, Cry1Ac, Cry1B, Cry1C, Cry1D, Cry1E, Cry1F, Cry1G, and Cry2A (Karim et al., 1997; Lee et al., 1997), but several different forms of each of these protein classes exist (e.g., today about 14 different Cry1C and about 20 different Cry1Ab forms have been reported in Crickmore et al. (1998) and in Crickmore et al. (2005)), and only one or a few of these were tested against rice insect pests. It is believed that no scientific publication describes the activity of the Cry1Ca4 protein to specific rice insect pests.

Also, Strizhov et al. (1998) describe the design of a synthetic gene encoding a Cry1Ca5 protein. After analyzing and comparing with the known proteins (Cry1Ca1, 2, 3, and 4; on page 18, line 3 to page 19, line 6) they conclude that the sequence of the Cry1Ca5 protein differs by amino acid replacement A124E from the Cry1Ca4 protein. Strizhov et al. (1998) conclude that the occurrence of glutamic acid at position 124 in Cry1Ca4 was clearly due to an error. Strizhov et al. (1998) also believe that the then known Cry1C sequences, including Cry1Ca4, contain critical errors with negative consequences either for function or stability of the Cry1C protein, had a corresponding synthetic gene been designed on the basis of the known wild-type DNA sequences. Yet, the current inventors succeeded in producing useful synthetic cry1C genes encoding an insecticidal Cry1C protein having a glutamic acid (Glu) amino acid at position 124, and in obtaining plants resistant to insects using such genes.

No rice plants containing a cry1C gene are commercially available. Tang et al. (2006) describe the development of insect-resistant transgenic indica rice with a synthetic gene encoding a Cry1Ca5 protein, but do not disclose the DNA sequence of the gene. The gene used in Tang et al. (2006) is said to be 84% identical to the native cry1Ca5 DNA, while the cry1C coding sequence of this invention is 69.7% identical to the native cry1Ca5 DNA of the same length when measured using the Needleman and Wunsch algorithm in EMBOSS with standard settings for the EDNAFULL matrix, and hence is quite different from the cry1Ca5 gene of Tang et al. (2006) (for the cry1C DNA sequence of SEQ ID No. 1, the sequence identity with the same length native cry1Ca5 DNA is only 55%, under the same settings). Also, the PCR primer set provided in Tang et al. (2006) will not allow detection of the cry1C coding region of the invention, illustrating the clear difference between that gene and the cry1C genes of the invention.

Strizhov et al. (1996) report the expression of a cry1Ca5 gene in alfalfa and tobacco. Cao et al. (1999) and Zhao et al. (2003) have described transgenic broccoli plants expressing a Cry1Ca5 Bt toxin, as well as crosses with broccoli plants expressing a Cry1Ac toxin, so that both the Cry1Ac and Cry1Ca5 toxins are expressed in the same plants. The cry1C coding sequence of this invention is only 78% identical to the coding sequence of the synthetic cry1Ca5 gene of Strizhov et al. (1996, Genbank accession number X99103) when measured using the Needleman and Wunsch algorithm in EMBOSS with standard settings for the EDNAFULL matrix (the DNA of SEQ ID No. 1 only has 61.1% sequence identity to the synthetic cry1Ca5 gene of Strizhov et al. using the same standard settings in EMBOSS).

The current invention provides new synthetic genes encoding a protein derived from the Cry1Ca4 Bt protein, which can be combined with a gene encoding a Bt Cry protein, such as Cry1Ab protein, for expression in plants, particularly rice. The DNA sequence of the cry1C genes of the invention do not occur in nature, and are different from any known DNA sequence.

OBJECTS AND SUMMARY OF THE INVENTION

In the current invention, several new insect control genes encoding proteins derived from Bt are provided for use in plants. Specifically, such genes are useful in rice, particularly plants of the species *Oryza sativa*. The plants or seeds comprising at least one of the new genes of the invention can be obtained by transformation of plant cells and production of plants or seeds therefrom comprising the genes of the invention. Also included herein are plants or seeds obtained by crossing a plant transformed to contain at least one of the genes of the invention with other plants, and by selection of those plants or seeds comprising the genes of the invention. Obviously, any plant species to be protected from insect species that are killed or controlled by the Bt proteins encoded by the novel genes of this invention can be transformed with the genes of the invention to obtain transgenic plants and seeds with increased resistance to such insects.

Also, the current invention provides novel Cry1C genes encoding an insecticidal protein comprising a functional plant intron in their coding sequence. The presence of the intron allows for high expression in plant cells, and at the same time secures that the gene does not express the insecticidal protein when the gene is contained in a prokaryotic (micro)organism, such as during cloning steps.

Also included in this invention is a DNA encoding a chloroplast transit peptide, particularly a DNA comprising the sequence of SEQ ID No. 3 from nucleotide position 7 to nucleotide position 372, particularly the sequence of SEQ ID No. 3.

In one embodiment of this invention, is provided the use of a synthetic, codon-optimized DNA sequence encoding a Cry1C protein or a protein comprising an insecticidal portion thereof, such as any insecticidal protein with at least 85%, particularly at least 90 or 95%, sequence identity to the protein of SEQ ID NO. 2 from amino acid position 28 to 627, with a glutamic acid at the amino acid position corresponding to position 124 in SEQ ID NO.2 (as can be determined using an amino acid sequence alignment), to control lepidopteran rice insect pests, particularly rice leaf folders or stem borers, as well as processes for controlling such insects comprising the step of transforming a plant with a chimeric gene comprising a plant-expressible promoter region operably-linked to such DNA sequence and sowing, planting or growing such plants in the field, or comprising the step of expressing such protein in plants, particularly rice plants.

The current invention also provides a plant transformed with a cry1C gene of the invention, which also comprises in its genome a DNA encoding a protein selected from the group consisting of: Cry1Ab, Cry1B, Cry1D, Cry1E, Cry1Aa, Cry1Ac, Cry11, Cry1J, Cry2A, Cry6B, Cry9C, Cry3A, a VIP3A toxin, a protease inhibitor such as cowpea trypsin inhibitor, protease inhibitor II, or a cystatin (e.g., the protease inhibitors of Xu et al., 1996 or Duan et al., 1996), the GNA lectin, or an insecticidal protein from *Xhenorhabdus, Serratia* or *Photorhabdus* species strains (e.g., Waterfield et al., 2001; (french-Constant and Bowen, 2000)), or hybrid or fusion Bt Cry proteins such as a Cry1A-hybrid toxin, e.g., the Cry1Ab-Cry1Ac fusion protein in rice event TT51 (Chinese patent application 200510062980, publication number 1840655) or the Cry1Ab/Cry1B fusion protein in Ho et al. (2006).

Also included herein are methods for controlling insects, comprising the step of planting or sowing in a field, plants comprising any of the chimeric genes or DNAs of this invention; as well as methods of controlling insects in *Oryza* species plants, comprising the step of expressing any of the above chimeric genes or DNA in plants; or methods of producing plants or seeds resistant to insects, comprising the steps of: a) obtaining a plant transformed with a cry1C chimeric gene of the invention, or transformed with a cry1C and cry1Ab chimeric gene of the invention, and b) selecting progeny of said plant or seeds thereof, containing said gene or DNA.

Also provided in accordance with this invention is a chimeric gene comprising the following operably-linked sequences: a) a first fragment of a coding sequence encoding an insecticidal protein, particularly an insecticidal protein derived from Bt or an insecticidal fragment or variant thereof, b) a monocot plant intron sequence, particularly derived from a monocot plant gene in which such intron is spliced, c) a second fragment of said coding sequence, d) a promoter region capable of directing expression in plant cells, and wherein the first and the second protein fragments are not insecticidal on their own, and wherein after splicing of said intron in a target plant cell, a functional insecticidal protein can be produced when said chimeric gene is transcribed and translated. Also provided herein are rice plant cells and rice plants comprising such chimeric gene. Particularly, from such chimeric gene no insecticidal protein can be produced in a given host cell in which the intron is not spliced, such as in a prokaryotic organism. In one embodiment, the intron is a rice or corn intron, such as an intron of the alcohol dehydrogenase-1 gene of *Zea mays.*

Provided herein is a chimeric cry1C gene, comprising the following operably-linked sequences:

a) a promoter region capable of directing expression in plant cells;

b) a DNA encoding an insecticidal Cry1C protein, comprising a DNA sequence with at least 95% sequence identity to the DNA sequence or the coding sequence of SEQ ID No. 1 from nucleotide position 82 to nucleotide position 2415, or to the DNA sequence or the coding sequence of SEQ ID No. 5 from nucleotide position 7 to nucleotide position 2784; and c) a 3' polyadenylation and transcript termination region; particularly such chimeric gene, wherein the insecticidal Cry1C protein comprises the amino acid sequence of SEQ ID No. 2 from amino acid position 28 to amino acid position 627, or comprises the amino acid sequence of SEQ ID No. 6 from amino acid position 3 to amino acid position 750, or comprises the amino acid sequence of a Cry1C protein, or a protein comprising an insecticidal portion thereof, with a glutamic acid at the amino acid position corresponding to position 124 in SEQ ID NO.2.

Also provided is the above chimeric cry1C gene, wherein said DNA encoding an insecticidal Cry1C protein comprises the DNA sequence or the coding sequence of SEQ ID No. 1 from nucleotide position 82 to nucleotide position 2415, the DNA sequence or the coding sequence of SEQ ID No. 5 from nucleotide position 7 to nucleotide position 2784, or comprises SEQ ID No. 1 or SEQ ID No. 5 or the coding sequence of SEQ ID No. 1 or SEQ ID No. 5; particularly such chimeric genes, wherein said insecticidal Cry1C protein comprises the amino acid sequence of SEQ ID No. 2 or SEQ ID No. 6.

In one embodiment, the promoter region in any one of the above chimeric cry1C genes comprises the sequence of any one of SEQ ID No. 9, 10, 13 or 14 or comprises the sequence of SEQ ID No. 9 from nucleotide position 1 to nucleotide position 1997, or an equivalent sequence differing in less than 1 to 5%, particularly less than 2%, of its nucleotides with any of such sequence. In one embodiment, the 3' polyadenylation and transcript termination region in a chimeric cry1C gene of the invention is from the octopine synthase gene of *Agrobacterium tumefaciens.*

Also provided herein is a DNA comprising any one of the above chimeric cry1C genes, further comprising a second chimeric gene, said second chimeric gene comprising the following operably-linked sequences:

a) a second promoter region capable of directing expression in plant cells;

b) a second coding region encoding an insecticidal Cry1Ab protein, such as a coding region comprising a DNA sequence with at least 95% sequence identity to the DNA sequence of SEQ ID No. 11 from nucleotide position 88 to nucleotide position 1851, and c) a 3' polyadenylation and transcript termination region; particularly such DNA comprising as second coding region a DNA sequence with at least 95% sequence identity to the DNA sequence of SEQ ID No. 11 from nucleotide position 7 to nucleotide position 1851, linked downstream (3') of the transit peptide coding sequence of SEQ ID No. 3 so that a fused coding region encoding a fusion protein is produced.

In one embodiment, the Cry1Ab protein in such DNA comprising a cry1C and cry1Ab chimeric gene, comprises an amino acid sequence with at least 99% sequence identity to the sequence of SEQ ID No. 12 from amino acid position 30 to amino acid position 617, to the sequence of SEQ ID No. 12 from amino acid position 3 to amino acid position 617, or to the sequence of SEQ ID No. 12, or is an insecticidal protein encoded by a DNA comprising the nucleotide sequence of SEQ ID No. 11 from nucleotide position 7 to nucleotide position 1851, or comprising the nucleotide sequence of SEQ ID No. 11 from nucleotide position 88 to nucleotide position 1851, or comprising the sequence of SEQ ID No. 11 operably-linked to (downstream of) the sequence of SEQ ID No. 3.

Also provided herein is such above DNA, wherein said second promoter region is different from the cry1C chimeric gene promoter region, and wherein said second promoter comprises the sequence of any one SEQ ID No. 9, 10, 13 or 14, or comprises the sequence of SEQ ID No. 9 from nucleotide position 1 to nucleotide position 1997, or an equivalent sequence differing in less than 1 to 5%, particularly less than 2%, of its nucleotides with any of such sequences.

Further provided in this invention is a transgenic plant cell or plant, comprising any one of the above chimeric cry1C genes or any one of the above DNAs comprising a cry1C and cry1Ab chimeric gene stably incorporated in its genome; as well as a transgenic plant cell or plant, comprising any one of the above cry1C chimeric genes, and a second chimeric gene comprising the following operably-linked sequences: a) a second promoter region capable of directing expression in plant cells; b) a second coding region encoding an insecticidal Cry1Ab protein, such as a coding region comprising a DNA sequence with at least 95% sequence identity to the DNA sequence of SEQ ID No. 11 from nucleotide position 88 to nucleotide position 1851, or at least 95% sequence identity to the DNA sequence of SEQ ID No. 11 from nucleotide position 7 to nucleotide position 1851, or at least 95% sequence identity to the DNA sequence of SEQ ID No. 11, and c) a second 3' polyadenylation and transcript termination region.

Also provided herein is such plant cell, comprising as second coding region a DNA sequence with at least 95% sequence identity to the DNA sequence comprising the nucleotide sequence of SEQ ID No. 11 from nucleotide position 7 to nucleotide position 1851, linked downstream (3') of the transit peptide coding sequence of SEQ ID No. 3, or a DNA comprising the nucleotide sequence of SEQ ID No. 3 from nucleotide position 7 to nucleotide position 372, so that a fused coding region encoding a fusion protein is produced; particularly such a plant cell, wherein said Cry1Ab protein comprises an amino acid sequence identical to or with at least 99% sequence identity to the sequence of SEQ ID No. 12 from amino acid position 30 to amino acid position 617, to the sequence of SEQ ID No. 12 from amino acid position 3 to amino acid position 617, or to the sequence of SEQ ID No. 12.

In one embodiment, any one of these above plant cells has a second promoter region which is different from the cry1C chimeric gene promoter region, and comprises the sequence of any one of SEQ ID No. 9 (or the sequence of SEQ ID No. 9 from nucleotide 1 to nucleotide 1997), 10, 13 or 14, particularly SEQ ID No. 13 or 14, or an equivalent sequence differing in less than 1 to 5%, particularly less than 2%, of its nucleotides with any of such sequences. In another embodiment, said cry1Ab chimeric gene comprises the 3' polyadenylation and transcript termination region of the octopine synthase gene from *Agrobacterium tumefaciens* (e.g., as described by De Greve et al., 1983).

Also provided herein are a plant or seed comprising any one of the above plant cells, particularly rice plant cells, as well as rice plants comprising such plant cells, particularly plants or seeds selected from the group consisting of a plant or seed of: corn, cotton, soybean, wheat, oilseed rape, sugarcane, soybean, cauliflower, cabbage, Chinese cabbage, turnip, mustard, oilseed rape, kale, and broccoli.

In one embodiment of this invention, seed, grain, or processed grain from such plants, particularly rice plants, comprising any one of the above chimeric cry1C genes, or comprising any one of the above chimeric cry1C genes and a chimeric cry1Ab gene (such as the above second chimeric gene) are provided.

Also provided herein is a plant, such as a rice plant, resistant to Lepidopteran plant insect pests, such as rice stem borers or rice leaf folders, comprising stably integrated in its genome, any one of the above chimeric cry1C genes or any one of the above chimeric cry1C genes and a chimeric cry1Ab gene (such as the above second chimeric gene), particularly such a plant is a rice plant which is resistant to *Chilo suppressalis, Marasmia patnalis, Scirpophaga incertulas, Sesamia inferens, Spodoptera litura* or *Cnaphalocrocis medinalis.*

Further provided herein is a method for controlling Lepidopteran plant insect pests, particularly rice stem borers or rice leaf folders, comprising: planting or sowing in a field, plants, particularly rice plants, comprising any one of the above cry1C chimeric genes or any one of the above chimeric cry1C genes and a cry1Ab chimeric gene (such as the above second chimeric gene), or a method for controlling rice stem borers or rice leaf folders, comprising: expressing any one of the above cry1C chimeric genes, or any one of the above chimeric cry1C genes and a cry1Ab chimeric gene (such as the above second chimeric gene) in a plant, such as a rice plant.

Also in accordance with the current invention is provided a process for obtaining a rice plant and progeny thereof resistant to *Chilo suppressalis, Marasmia patnalis, Cnaphalocrocis medinalis, Sesamia inferens, Spodoptera litura* or *Scirpophaga incertulas*, comprising transforming a rice plant with any one of the above chimeric cry1C genes or any one of the above chimeric cry1C genes and a cry1Ab chimeric gene (such as the above second chimeric gene), and obtaining progeny thereof comprising such gene or genes.

A method of producing plants or seeds resistant to insects is also provided herein, comprising the steps of: a) obtaining a plant transformed with any one of the above chimeric cry1C genes or any one of the above chimeric cry1C genes and a chimeric cry1Ab gene (such as the above second chimeric gene), and b) selecting progeny of said plant, or seeds thereof containing said gene or genes, such as by using specific primers or probes.

Also provided herein is a microorganism comprising any one of the above chimeric cry1C genes, or the coding sequence thereof, or any one of the above DNAs comprising a chimeric cry1C gene and a chimeric cry1Ab gene (such as the above second chimeric gene), or the coding sequences thereof, particularly of the genus *Escherichia, Bacillus* or *Agrobacterium.*

Also provided herein is the use of any one of the above chimeric cry1C genes or any one of the above chimeric cry1C genes and a chimeric cry1Ab gene (such as the above second chimeric gene), to control insect pests, as well as the use of any one of the above chimeric cry1C genes or any one of the above chimeric cry1C genes and a chimeric cry1Ab gene (such as the above second chimeric gene) to obtain plants, particularly rice plants, protected from Lepidopteran plant insect pests, particularly *Chilo suppressalis, Marasmia patnalis, Cnaphalocrocis medinalis, Sesamia inferens, Spodoptera litura* or *Scirpophaga incertulas*.

Further, in accordance with this invention are provided methods for detecting the presence of the cry1C coding sequence of the invention in biological, such as plant, material, e.g. in rice grain or seeds, or rice products, comprising the step of using specific oligonucleotide primers or probes, such as PCR primers specific for the cry1C coding region of the invention, such as primers comprising the sequence of SEQ ID No. 7 or 8. Also provided herein is a kit, comprising two primers specifically recognizing the sequence of SEQ ID No. 1, such as a kit comprising a first primer comprising the sequence of SEQ ID No. 7 and a second primer comprising the sequence of SEQ ID No. 8.

Further provided herein is a method for controlling Lepidopteran rice insect pests, comprising: expressing in rice plants an insecticidal Cry1C protein and an insecticidal Cry1Ab protein, wherein said Cry1C protein comprises the amino acid sequence of SEQ ID No. 2 from amino acid position 28 to amino acid position 627, particularly wherein said Cry1Ab protein comprises an amino acid sequence with at least 99% sequence identity to the sequence of SEQ ID No. 12 from amino acid position 30 to amino acid position 617. Particularly provided herein is such method wherein said rice insects are *Chilo suppressalis, Marasmia patnalis, Cnaphalocrocis medinalis, Sesamia inferens, Spodoptera litura* or *Scirpophaga incertulas*, and wherein said Cry1Ab protein comprises the amino acid sequence of SEQ ID No. 12 from amino acid position 30 to amino acid position 617.

Also provided herein is the use of a DNA encoding an insecticidal Cry1C protein comprising the amino acid sequence of SEQ ID No. 2 from amino acid position 28 to amino acid position 627, to obtain rice plants protected from *Chilo suppressalis, Marasmia patnalis, Cnaphalocrocis medinalis, Sesamia inferens, Spodoptera litura* or *Scirpophaga incertulas*.

DESCRIPTION

In accordance with this invention, a "nucleic acid sequence" refers to a DNA or RNA molecule in single or double stranded form, preferably a DNA molecule. An "isolated DNA", as used herein, refers to a DNA which is not naturally-occurring or no longer in the natural environment wherein it was originally present, e.g., a DNA coding sequence associated with other regulatory elements in a chimeric gene, a DNA transferred into another host cell, such as a plant cell, or an artificial, synthetic DNA sequence having a different nucleotide sequence compared to any known naturally-occurring DNA sequence.

In accordance with this invention, nucleic acid sequences, particularly DNA sequences, encoding Bt Cry toxins or variants thereof have been constructed. The new DNA sequences are designated herein as cry1C, and their encoded proteins are designated herein as Cry1C (e.g., Cry1C1 or Cry1C2), proteins. Also a new DNA sequence encoding an optimized chloroplast transit peptide is provided herein, e.g., a DNA comprising the sequence of SEQ ID No. 3 from nucleotide position 7 to nucleotide position 371, particularly the sequence of SEQ ID No. 3.

As used herein, the term "Cry1C protein of the invention" refers to any insecticidal protein comprising the smallest fragment of the amino acid sequence of SEQ ID No. 2 which retains insecticidal activity (hereinafter referred to as "smallest toxic fragment"), particularly any protein comprising an amino acid sequence with at least 99% sequence identity to, or identical to, the amino acid sequence from the amino acid at position 28 to the amino acid at position 627 in SEQ ID No. 2, preferably any insecticidal protein comprising an amino acid sequence with at least 99% sequence identity to, or identical to, the amino acid sequence of SEQ ID No. 2 from amino acid position 2 to amino acid position 627, particularly such proteins (or any Cry1C protein, such as any insecticidal protein comprising at least 85%, particularly at least 90 or 95%, sequence identity to the sequence of SEQ ID No. 2 from amino acid position 28 to 627) that contain a Glu amino acid at amino acid position 124 in SEQ ID No. 2, or at the equivalent position in a shorter or longer sequence (as can be determined in an amino acid sequence alignment). Also included in this definition is an insecticidal protein comprising the amino acid sequence of SEQ ID No. 2 from amino acid position 1 to amino acid position 627, or comprising the amino acid sequence of SEQ ID No. 2 (named Cry1C1 protein herein), as well as an insecticidal protein comprising the amino acid sequence of SEQ ID No. 5 from amino acid position 3 to amino acid position 627, or comprising the amino acid sequence of SEQ ID No. 5 (also named Cry1C2 protein herein), as well as such insecticidal proteins wherein 1-5 amino acids have been deleted or replaced by other amino acids, without changing the Glu amino acid at amino acid position 124 in SEQ ID No. 2 or at an equivalent position in a shorter or longer protein.

Also included herein as a Cry1C protein of the invention are minor amino acid additions such as the insertion of an Ala or Asp amino acid between the first and second amino acid of a Cry1C protein of the invention, to give Met Ala or Met Asp as first two amino acids, or the fusion of a Cry1C protein of the invention to another protein or peptide, such as a transit peptide-Cry1C fusion protein.

Since some changes to the Cry1C amino acid sequence are possible without changing it's insecticidal activity (such as, e.g., the introduction of DNA restriction enzyme cleavage sites for manufacturing of the gene encoding the Cry1C protein), also included in the invention as a Cry1C protein as used herein is any protein comprising an equivalent of the amino acid sequence from the amino acid at position 28 to the amino acid at position 627 in SEQ ID No. 2, but wherein less than 10, preferably 1 to 5, amino acids are replaced by other amino acids in this region in SEQ ID No. 2, without negatively affecting the insecticidal activity of the protein. Preferably, the amino acid at position 124 in SEQ ID No. 2 or at position 247 in SEQ ID No. 5 (or at an equivalent position in a shorter or longer sequence) is glutamic acid (Glu) in such protein.

Also useful in this invention are variants of the Cry1C protein of SEQ ID No. 2 which comprise a sequence having a sequence identity of at least 95%, particularly at least 96%, 97%, 98% or at least 99% at the amino acid sequence level with the region from the amino acid at position 28 to the amino acid at position 627 of SEQ ID No. 2, as determined using the Needleman-Wunsch global alignment algorithm in EMBOSS (Rice et al., 2000) to find optimum alignment over the entire length of the sequences, using default settings (gap opening penalty 10, gap extension penalty 0.5; for amino acid sequence comparisons, the EBLOSUM62 matrix is used). Preferred variants of the Cry1C protein of the invention include a protein comprising the sequence of SEQ ID No. 2 from amino acid position 28 to amino acid position 627, but wherein one, some or all of the following amino acids at the following positions compared to the positions in SEQ ID No. 2 are changed: the amino acid at position 183 is Valine, the amino acid at position 294 is Arginine, the amino acid at position 453 is Aspartic acid, or the amino acid at position 592 is Arginine. Particularly, variants of the Cry1C protein of this invention have no more than 5 amino acid differences with the Cry1C protein of SEQ ID No. 2 from amino acid position 28 to amino acid position 627, and retain the Glu amino acid at position 124 in SEQ ID No. 2 (or at an equivalent position in a shorter or longer sequence).

A Cry1C protein comprising the amino acid sequence from the amino acid at position 28 to the amino acid at position 627 in SEQ ID No. 2 retains all or most of the insecticidal activity to its' target insects which are killed or who's growth is inhibited by the entire protein as produced by *Bacillus thuringiensis* in nature, and addition of amino acids or protein sequences at the N- or C-terminal part thereof does not disrupt this insecticidal activity. Hence, any protein characterized by an amino acid sequence containing or including this region is useful and forms part of this invention.

The terminology DNA or protein "comprising" a certain sequence X, as used herein, refers to a DNA or protein including or containing at least the sequence X, so that other nucleotide or amino acid sequences can be included at the 5' (or N-terminal) and/or 3' (or C-terminal) end, e.g. (the nucleotide sequence of) a selectable marker protein as disclosed in EP 0 193 259, (the nucleotide sequence of) a transit peptide, and/or a 5' leader sequence or a 3' trailer sequence. Similarly, use of the term "comprise", "comprising" or "comprises" throughout the text and the claims of this application should be understood to imply the inclusion of a stated integer or step or group of integers or steps but not the exclusion of any other integer or step or group of integers or steps.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other, is regarded as a position with non-identical residues. The alignment of the two sequences is performed by the Needleman and Wunsch algorithm (Needleman and Wunsch 1970) in EMBOSS (Rice et al., 2000) to find optimum alignment over the entire length of the sequences, using default settings (gap opening penalty 10, gap extension penalty 0.5).

The "smallest toxic fragment" of a Cry1C protein of the invention, as used herein, is that smallest fragment or portion of a Cry1C protein retaining insecticidal activity that can be obtained by enzymatic, such as trypsin or chymotrypsin, digestion of the full length Cry protein, or that smallest fragment or portion of a Cry protein retaining insecticidal activity that can be obtained by making nucleotide deletions in the DNA encoding a Cry1C protein. Such smallest toxic fragment can also be obtained by treatment of a Cry1C protein with insect gut juice, preferably midgut juice, from an insect species susceptible to (i.e., killed or otherwise negative affected in its growth or feeding by) such Cry1C protein.

As used herein, the terms "cry1C DNA" or "cry1C gene", refer to any DNA sequence encoding the Cry1C protein of the invention. This includes naturally occurring, artificial or synthetic DNA sequences encoding the Cry1C protein of the invention, such as a DNA identical to or with at least 95%, 97%, 98%, or 99% sequence identity to the DNA or coding sequence of SEQ ID No. 1 from nucleotide position 82 to nucleotide position 2415, or to the DNA sequence or coding sequence of SEQ ID No. 1 from nucleotide position 4 to 2415, or to the DNA or coding sequence of SEQ ID No. 1, or to the DNA or coding sequence of SEQ ID No. 5 from nucleotide position 7 to nucleotide position 2784, or to the DNA or coding sequence of SEQ ID No. 5 from nucleotide position 1 to nucleotide position 2784, or to the DNA or coding sequence of SEQ ID No. 5. Also included herein are DNA sequences encoding insecticidal proteins which are similar enough to any one of the DNA sequences of SEQ ID Nos. 1 or 5 so that they can (i.e., have the ability to) hybridize to these DNA sequences under stringent hybridization conditions. "Stringent hybridization conditions", as used herein, refers particularly to the following conditions: immobilizing the relevant DNA sequences on a filter, and prehybridizing the filters for either 1 to 2 hours in 50% formamide, 5% SSPE, 2×Denhardt's reagent and 0.1% SDS at 42° C., or 1 to 2 hours in 6×SSC, 2×Denhardt's reagent and 0.1% SDS at 68° C. The denatured dig- or radio-labeled probe is then added directly to the prehybridization fluid and incubation is carried out for 16 to 24 hours at the appropriate temperature mentioned above. After incubation, the filters are then washed for 30 minutes at room temperature in 2×SSC, 0.1% SDS, followed by 2 washes of 30 minutes each at 68° C. in 0.5×SSC and 0.1% SDS. An autoradiograph is established by exposing the filters for 24 to 48 hours to X-ray film (Kodak XAR-2 or equivalent) at −70° C. with an intensifying screen. Of course, equivalent conditions and parameters can be used in this process while still retaining the desired stringent hybridization conditions.

Also included herein as cry1C genes of the invention are DNA sequences encoding an insecticidal protein with at least 80% or 90%, preferably at least 93 to 97%, particularly at least 95, at least 98 or at least 99%, sequence identity to the DNA sequence of SEQ ID No. 1 from nucleotide position 82 to nucleotide position 2415, or to the DNA sequence of SEQ ID No. 1 from nucleotide position 4 to 2415, or to the DNA sequence of SEQ ID No. 1, or to the DNA sequence of SEQ ID No. 5 from nucleotide position 7 to nucleotide position 2784, or to the DNA sequence of SEQ ID No. 5, particularly a DNA encoding a Cry1C protein comprising an amino acid sequence with at least 95%, 97%, 98%, or 99% sequence identity with the amino acid sequence from amino acid position 2 or 28 to the amino acid at position 627 in SEQ ID No. 2, or with the amino acid sequence of SEQ ID No. 2 or 5, particularly such Cry1C protein wherein the amino acid at position 124 in SEQ ID No. 2 (or at an equivalent position in another sequence) is Glu. The DNA sequence identities referred to herein are calculated using the Needleman-Wunsch global alignment algorithm in EMBOSS (Rice et al., 2000) to find optimum alignment over the entire length of the sequences, using default settings (gap opening penalty 10, gap extension penalty 0.5; for DNA sequence comparisons, the EDNAFULL matrix is used; for amino acid sequence comparisons, the EBLOSUM62 matrix is used).

In one embodiment, the term "cry1C DNA (or gene) of the invention", refers to any DNA (or gene) sequence encoding an insecticidal protein, particularly an insecticidal Cry1C protein, comprising: a) the nucleotide sequence of SEQ ID No. 1 from nucleotide position 82 to nucleotide position 2415, b) the nucleotide sequence of SEQ ID No. 5 from nucleotide position 7 to nucleotide position 2784, c) the nucleotide sequence of SEQ ID No. 1 from nucleotide position 4 to nucleotide position 2415, d) the nucleotide sequence of SEQ ID No. 1 from nucleotide position 82 to nucleotide position 590 linked to the nucleotide sequence from nucleotide position 1125 to nucleotide position 2415 in SEQ ID No. 1, or e) the nucleotide sequence of SEQ ID No. 5 from nucleotide position 7 to nucleotide position 959 linked to the nucleotide sequence from nucleotide position 1794 to nucleotide position 2784 in SEQ ID No. 5, or f) the coding sequence of any one of the nucleotide sequence of a) to c) above. In one embodiment, a cry1C DNA of the invention is the cry1C1 DNA of SEQ ID No. 1 or the cry1C2 DNA sequence of SEQ ID NO. 5.

In another embodiment, a cry1C DNA of the invention refers to any DNA encoding an insecticidal protein, particularly an insecticidal Cry1C protein, hybridizing under stringent hybridization conditions to a DNA comprising: a) the nucleotide sequence of SEQ ID No. 1 from nucleotide position 82 to nucleotide position 2415, b) the nucleotide sequence of SEQ ID No. 5 from nucleotide position 7 to nucleotide position 2784, c) the nucleotide sequence of SEQ ID No. 1 from nucleotide position 4 to nucleotide position 2415, or d) the coding sequence of the nucleotide sequences of any one of a) to c), or any DNA with at least 80% or 90%, preferably at least 93 to 97%, particularly at least 95, at least 98 or at least 99%, sequence identity to a DNA comprising: a) the nucleotide sequence of SEQ ID No. 1 from nucleotide position 82 to nucleotide position 2415, b) the nucleotide sequence of SEQ ID No. 5 from nucleotide position 7 to nucleotide position 2784, c) the nucleotide sequence of SEQ ID No. 1 from nucleotide position 4 to nucleotide position 2415, or d) the coding sequence of the nucleotide sequences of any one of a) to c).

"Insecticidal activity" of a protein, as used herein, means the capacity of a protein to kill insects, inhibit their growth or cause a reduction in insect feeding when such protein is ingested by insects. In this invention, such ingestion is preferably through ingestion of recombinant host cells, such as a plant cell, seed or plant, expressing a protein of the invention, by such insect. It is understood that activity to insects of one insect species, preferably the larvae thereof, is sufficient for a protein to have insecticidal activity as used herein, although often insects of different insect species are affected by the proteins of the invention. The recombinant hosts expressing a Cry1C protein of the invention are typically developed for or targeted to specific major insect pest species for a certain crop or region where such insect species is a pest, e.g., the Lepidopteran rice stem borers and leaf-folders which are insect pests on rice crops in China, India, Indonesia, Vietnam, Pakistan, Bangladesh, Myanmar, and Thailand, but other insects can also be controlled by the recombinant hosts of the invention, such as by the transgenic plant cells or plants, e.g., the transgenic rice plant cells or plants of the invention comprising any one of the chimeric cry1C genes of the invention.

The plants of the invention containing a cry1C gene of the invention allow new methods of agriculture to be used, wherein less or no insecticides are used on plants such as rice to control plant insect pests, such as rice stem borers or rice leaf-folders, and one embodiment of the invention hence includes use of the plants or plant cells of the invention, such as rice plants or plant cells, comprising a cry1C gene of the invention to control plant pest insects, such as rice pest insects, particularly rice stem borers and rice leaf-folders, as well as methods of controlling plant insect pests, such as rice insect pests, e.g., rice stem borers and rice leaf-folders, by expressing the Cry1C protein of the invention in plant cells, seeds or plants, particularly rice plant cells, seeds or plants, or by growing, sowing or cultivating plants, such as rice plants, comprising the cry1C gene of the invention.

"(Insect-)controlling amounts" of or "control" by a Cry1C protein, or by a recombinant host expressing a Cry1C protein of this invention, as used herein, refers to an amount of protein which is sufficient to limit damage to a plant by insects feeding on such plant, e.g., by killing the insects or by inhibiting the insect development, fertility or growth in such a manner that an insect species provides less damage to a plant. This does not mean that treatment of plants with chemical insecticides will no longer be necessary (e.g., to control insect species not affected by the proteins of the invention, such as (secondary) Coleopteran or Dipteran insect pests), but that treatment by chemical insecticides for the insects targeted by the proteins of the invention can be significantly reduced or avoided, while still obtaining acceptable plant performance in the field and acceptable yield.

The cry1C genes of the invention are preferably used in rice cells, plants, or seeds to control rice insect pests. "Rice", as used herein, refers to a cereal grass of the genus *Oryza* which is cultivated for its edible grain, preferably *Oryza sativa* and *Oryza glaberrima*, particularly *Oryza sativa*. "Rice grain", as used herein, includes brown or unpolished rice grain, polished or white rice grain, as well as steamed, fried or cooked, broken or parboiled grain as well as pre-germinated rice grain. Rice as used herein includes any manner of production or growing of rice, such as irrigated or non-irrigated rice, floating or deepwater rice, paddy rice, dry land rice, open pollinated or hybrid rice, and includes rice of the indica, japonica or javonica cultivars. Hybrid rice, particularly Arize™ hybrid rice, is a preferred embodiment of this invention, because of its' higher grain yield, and optimal grain and seed quality. Rice, when used herein generally, also refers to seeds, cells, protoplasts, pollen, or any parts or tissues of a rice plant.

As used herein, "processed rice grain" refers to milled, polished, dehusked, parboiled, converted, broken, steamed, or cooked grain. Included herein as processed rice grain is also (partially) cooked or steamed brown rice, such as quick or instant brown rice, and any type of rice grain no longer containing a viable embryo that can grow into a rice plant.

"Rice products", as used herein, refers to products containing or made from rice plants, seeds, cells or grain of the invention, including rice flour, noodles, porridge, beverages, rice dishes and the like.

In accordance with this invention, insects susceptible to the Cry1C proteins of the invention are contacted with these proteins in insect-controlling amounts, preferably insect-killing amounts. In one embodiment of this invention, recombinant hosts of the invention, such as transgenic plant cells or plants of the invention, express a protein or a combination of proteins of the invention at high levels, such that a "high dose" level is obtained. A "high dose level", "high dose insect resistance" or "high dose" expression, as used herein when referring to a recombinant plant cell or plant, refers to a concentration of the insecticidal protein in a plant cell or plant (measured by ELISA as a percentage of the total soluble protein, which total soluble protein is measured after extraction of soluble proteins in an extraction buffer (e.g., the extraction buffer described in Jansens et al., 1997) using Bradford analysis (Bio-Rad, Richmond, Calif.; Bradford, 1976)) which kills a developmental stage of the target insect which is significantly less susceptible, preferably at least 25 times less susceptible to the toxin than the first larval stage of the insect, and can thus can be expected to ensure full control of the target insect. In one embodiment this refers to the obtaining of at least 97 percent, preferably at least 99 percent, most preferably 100 percent, mortality for the fourth larval instar (for insects having 5 larval instars) or the last larval instar (for insects having 4 or less larval instars) of a target insect, as measured 10 to 14 days after insect infestation of such plant cells or plants, or parts thereof, in routine insect bioassays (using a normal susceptible insect colony (not insects selected for resistance to Bt proteins)), preferably whole plant insect bioassays, using suitable controls.

The existence of one target insect species (i.e., an insect species, preferably the larvae thereof, which can cause significant damage to a plant species, and which is typically an insect for which a transgenic plant is designed and developed) for which transformed plant cells or plants according to this invention provide a "high dose" level insect resistance is sufficient for a plant to be designated as giving "high dose" expression, in accordance with this invention.

Preferred target insects for the plants and plant cells of this invention are economically damaging Lepidopteran insect pests of plants that feed on or otherwise damage plants and thereby reduce plant yields (herein referred to as "Lepidopteran plant insect pests"), particularly Lepidopteran rice stem borers and rice leaf-folders, preferably insects selected from the group consisting of: the striped stem borer *Chilo suppressalis*, the yellow stem borer *Scirpophaga incertulas* (also named *Tryporyza incertulas*), the white stem borer *Scirpophaga innotata* (also named *Tryporyza innotata*), the dark-headed stem borer *Chilo polychrysa*, the pink stem borer *Sesamia inferens*, the sugarcane borer *Diatraea saccharalis*, the rice stalk borer *Chilo plejadellus*, the rice leaffolder *Marasmia patnalis*, the rice leaffolder *Cnaphalocrocis medinalis*, and insects such as *Hereitogramma licarisalis, Naranga aenescens, Mycalesis gotama, Marasmia exigua, Marasmia ruralis, Nymphula depunctalis, Spodoptera litura, Rupela albinella, Spodoptera frugiperda, Mythimna unipuncta, Chilo zacconius* and *Pamara guttata*. Most particularly target insects for the Cry1C plants, cells or seeds of this invention are rice insect pest species of the following genera: *Chilo, Scirpophaga, Marasmia, Cnaphalocrocis, Diatraea*, and *Spodoptera*, preferably *Chilo suppressalis, Scirpophaga incertulas, Marasmia patnalis, Cnaphalocrocis medinalis*, and *Spodoptera litura* insects. Obviously, in different countries or regions, different local names can be used for the insect of the same species.

A "chimeric gene", as used herein, is used to refer to a DNA comprising at least two different DNA fragments (such as a promoter, a 5' untranslated leader, a coding region encoding a chloroplast transit peptide, a cry1C coding region, an intron, a 3' untranslated trailer, and a 3' end transcript formation and polyadenylation region) which are operably-linked and which are not naturally associated with each other or which originate from different sources, preferably this term refers to a DNA comprising a plant-expressible promoter region operably-linked to a DNA sequence encoding a Cry1C protein of this invention, such as the DNA or coding sequence of SEQ ID No. 1 or 5.

A "coding sequence" or "coding region" as used herein, when referring to the cry1C gene of the invention, refers to that DNA sequence encoding an amino acid sequence and excludes any 5' or 3' untranslated leader or trailer sequences, or untranslated sequences such as introns. Hence, the coding sequence of SEQ ID No. 1 is the DNA sequence from nucleotide position 1 to 590 in SEQ ID No. 1 linked to the DNA sequence from nucleotide position 1125 to 2415, which forms one continuous reading frame encoding one protein, not interrupted by untranslated parts such as introns or stop codons. A coding sequence, as used herein, excludes a stop codon, but includes the (Met) translation start codon.

The term "encoding", as used herein, like in the terminology "a gene or DNA encoding protein X", refers to the capacity of such gene to produce a protein upon transcription and translation of the coding sequence contained in such gene in a target host cell. Hence, the cry1C1 chimeric gene of the invention encodes the Cry1C1 protein of the invention, even though this chimeric gene contains two coding sequences (or exons) interrupted by a non-coding intron sequence.

The DNAs encoding the Cry1C proteins of the invention can be chemically synthesized using routine techniques, and can be inserted in expression vectors to produce high amounts of Cry1C proteins. The Cry1C proteins of the invention can be used to prepare specific monoclonal or polyclonal antibodies in a conventional manner (Höfte et al., 1988) to develop immuno-assays (e.g., ELISA, Western blotting, antibody-coated dip-sticks) to detect the presence of absence of these proteins in any material, such as plant material.

The tools developed to identify transgenic plant cells, plants, or plant-derived materials such as leaves, seeds, grain, or rice products comprising any one of the cry1C genes of the invention, or DNA-containing products which comprise or are derived from plant material comprising a cry1C gene of the invention are based on the specific sequence characteristics of the novel genes of the invention, such as, a specific restriction map of the genomic region comprising the introduced (foreign) cry1C gene, or specific molecular markers based on the sequence of the foreign DNA integrated in the plant's genome.

Once the sequence of a foreign DNA such as the cry1C genes of the invention is known, primers and probes can be developed which specifically recognize these sequences in the nucleic acid (DNA or RNA) of a sample by way of a molecular biological technique. For instance a PCR method can be developed to identify the genes of the invention in biological samples (such as samples of plants, plant material or products comprising plant material, such as rice grain or seed or rice products as defined herein). Such a PCR is based on at least two specific "primers", e.g., both recognizing a sequence within the cry1C DNA or the cry1C coding region of the invention (such as the DNA of SEQ ID No. 1 or 5, or the coding region of SEQ ID No. 1 or 5), or one recognizing a sequence within the cry1C DNA and the other recognizing a sequence within the associated transit peptide sequence or within the regulatory regions such as the promoter or 3' end of the chimeric gene comprising a cry1C DNA of the invention. The primers preferably have or comprise a sequence of between 15 and 35 nucleotides which under optimized PCR conditions specifically recognize a sequence within the cry1C chimeric gene or coding region of the invention, so that a specific fragment ("integration fragment" or discriminating amplicon) is amplified from a nucleic acid sample comprising a cry1C gene of the invention. This means that only the targeted integration fragment, and no other sequence in the plant genome or foreign DNA, is amplified under optimized PCR conditions.

PCR primers suitable for the invention are oligonucleotides ranging in length from 17 nucleotides to about 200 nucleotides, comprising a nucleotide sequence of at least 17 consecutive nucleotides, preferably 20 consecutive nucleotides, selected from the cry1C DNA or cry1C chimeric gene sequence as transferred to plant cells or plants of the invention.

The primers may of course be longer than the mentioned 17 consecutive nucleotides, and may, e.g., be 20, 21, 22, 30, 35, 50, 75, 100, 150, 200 nt long or even longer. The primers may entirely consist of nucleotide sequences selected from the cry1C nucleotide sequences. However, the nucleotide sequence of the primers at their 5' end (i.e., outside of the 3'-located 17 consecutive nucleotides) is less critical. Thus, the 5' sequence of the primers may consist of a nucleotide sequence selected from the cry1C chimeric gene sequence, as appropriate, but may contain several (e.g., 1, 2, 5, 10) mismatches. The 5' sequence of the primers may even entirely consist of a nucleotide sequence unrelated to the cry1C genes of the invention, such as a nucleotide sequence representing one or more restriction enzyme recognition sites. Such unrelated sequences or flanking DNA sequences with mismatches should preferably be no longer than 100, more preferably no longer than 50 or no longer than 25 nucleotides.

Moreover, suitable primers may comprise or consist of a nucleotide sequence at their 3' end spanning the joining region between the cry1C coding sequence of the invention and the associated transit peptide sequence or the regulatory elements in the cry1C chimeric gene integrated in the plant DNA, such as a promoter sequence, a leader sequence, a trailer sequence or a 3' transcript termination and polyadenylation sequence. It will also be immediately clear to the skilled artisan that properly selected PCR primer pairs should also not comprise sequences complementary to each other.

The term "primer" as used herein encompasses any nucleic acid that is capable of priming the synthesis of a nascent nucleic acid in a template-dependent process, such as PCR. Typically, primers are oligonucleotides from 10 to 30 nucleotides, but longer sequences can be employed. Primers may be provided in double-stranded form, though the single-stranded form is preferred. Probes can be used as primers, but are designed to bind to the target DNA or RNA and need not be used in an amplification process.

The term "recognizing" as used herein when referring to specific primers, refers to the fact that the specific primers specifically hybridize to a nucleic acid sequence in the cry1C genes of the invention under a standard PCR identification protocol, whereby the specificity is determined by the presence of positive and negative controls as is well known in the art.

Also included herein is a kit to detect the cry1C genes of the invention in biological material, as well as the use of such kit to screen biological material. A "kit" as used herein refers to a set of reagents for the purpose of performing the identification of the cry1C genes of the invention in biological samples. More particularly, a preferred embodiment of the kit of the invention comprises at least one or two specific primers, as described above. Optionally, the kit can further comprise any other reagent described herein in the PCR identification protocol. Alternatively, according to another embodiment of this invention, the kit can comprise a specific probe, as described above, which specifically hybridizes with nucleic acid of biological samples to identify the presence of the cry1C genes therein. Optionally, the kit can further comprise any other reagent (such as but not limited to hybridizing buffer, label) for identification of the cry1C genes in biological samples, using the specific probe.

Standard PCR protocols are described in the art, such as in 'PCR Applications Manual" (Roche Molecular Biochemicals, 2nd Edition, 1999). The optimal conditions for the PCR, including the sequence of the specific primers, is specified in a PCR identification protocol for each cry1C gene-containing plant species. It is however understood that a number of parameters in the PCR identification protocol may need to be adjusted to specific laboratory conditions, and may be modified slightly to obtain similar results. For instance, use of a different method for preparation of DNA may require adjustment of, for instance, the amount of primers, polymerase and annealing conditions used. Similarly, the selection of other primers may dictate other optimal conditions for the PCR identification protocol. These adjustments will however be apparent to a person skilled in the art, and are furthermore detailed in current PCR application manuals such as the one cited above.

Examples of suitable primer combinations in accordance with the invention for detecting the cry1C DNA of the invention are a primer comprising the sequence of SEQ ID No. 7 (primer P1C203) and a primer comprising the sequence of SEQ ID No. 8 (primer P1C204). Hence, any DNA encoding an insecticidal Cry1C protein which is specifically recognized by these primers is included in this invention, as well as any methods or any kits to detect such DNA using these or other specific primers. The primers P1C203 and P1C204, or primers comprising the sequence of SEQ ID No. 7 or 9, can also be used as probes for detecting the presence of a cry1C gene of the invention.

Also specific markers or labeled probes can be designed to detect the DNA sequences of this invention, and any use of specific markers or probes directed to any of the cry1C genes of the invention is included herein. In one embodiment of this invention, the specific markers, primers or labeled probes do not detect or recognize any plant, preferably any plant of the same species as the test plant, not containing a cry1C DNA sequence of the invention, particularly any such markers, primers or labeled probes do not detect or recognize any plant expressing a Cry1C protein wherein such plant does not contain a DNA sequence of the invention (such as a cry1C DNA as defined herein, e.g., a DNA comprising the nucleotide sequence of any one of SEQ ID No. 1 or 5, or the coding sequence of SEQ ID No. 1 or 5).

The DNA sequences of this invention can be slightly modified to allow for more convenient restriction enzyme sites, or to make small changes without changing the efficacy and wherein such DNA encodes a protein with the same or substantially the same insecticidal activity as the Cry1C protein of the invention. Indeed, because of the degeneracy of the genetic code, it is well known that most amino acid codons can be replaced by others without changing the amino acid sequence of the protein. Furthermore, some amino acids can be substituted by other equivalent amino acids or can be added without significantly changing the insecticidal activity of the protein. Equivalents of the DNA sequences of the invention include DNA sequences with less than 20, preferably 5-10, nucleotide differences compared to the cry1C genes or coding sequences of this invention as defined herein, but which encode an insecticidal Cry1C protein of the invention, as defined herein.

With the term "substantially the same", when referring to the amino acid sequence of a Cry1C protein of this invention, is meant to include an amino acid sequence that differs in no more than 5%, preferably no more than 2%, particularly no more than 1% to the amino acid sequence of the protein compared to; and when referring to toxicity or insecticidal activity of a Cry1C protein, is meant to include a protein whose LC50 value obtained under the same conditions of bio-assay (preferably in the same bio-assay using insects from the same population and suitable controls) differs no more than 2 times, preferably no more than 50%, of the LC50 value obtained for the protein compared to.

"Microorganism", as used herein, refers to any living organism that can be observed only with the aid of a microscope, such as bacteria, yeast cells, plant cells, viruses, fungi. This includes all generally unicellular organisms with dimensions beneath the limits of vision which can be propagated and manipulated in a laboratory, typically prokaryotic or unicellular eukaryotic life forms, including tissue cultures and plasmids.

By an "insecticidally effective part (or portion or fragment)" of a DNA sequence encoding a Cry1C protein, is meant a DNA sequence encoding a polypeptide which has fewer amino acids than the Cry1C protoxin as produced in nature by Bt but which is still insecticidal.

In order to express all or an insecticidally effective part of the DNA sequence encoding a Cry protein of this invention in a microorganism or a recombinant host, e.g., *E. coli*, a Bt strain, a plant or plant cells, suitable restriction sites can be introduced, flanking the DNA sequence. This can be done by site-directed mutagenesis, using well-known procedures (Stanssens et al., 1989; White et al., 1989).

For obtaining enhanced expression in plants and/or preventing expression of an insecticidal protein when not present in a plant host cell (such as in a bacterial or other prokaryote host cell), in one embodiment of the invention a plant intron, preferably a monocot plant intron, is inserted in the chimeric cry1C genes of the invention, preferably in the coding sequence. Any of the known plant introns, preferably monocot plant introns, (e.g., Brown, 1986, Brown and Simpson, 1998, Brown et al., 1996) can be used herein as long as the intron is operably-linked to the coding sequence fragments so as to assure proper splicing in plant cells. Operable linkage of the intron and the resulting proper splicing is conveniently checked in the target host plant species or cells thereof by checking the production of an active protein, by RT-PCR, Northern blot or by any other means available in the art. In a preferred embodiment, the intron of the invention is a monocot intron, such as the Adh1 intron described by Dennis et al. (1984), e.g., the nucleotide sequence of SEQ ID No. 1 from nucleotide position 591 to nucleotide position 1124. In another embodiment of the invention, the intron contained in the insecticidal protein coding sequence, particularly the Cry1C coding sequence, is the second intron of the light-inducible tissue-specific ST-LS1 gene of *Solanum tuberosum* (potato) as described by Eckes et al. (1986).

In one embodiment of this invention a plant intron is operably-linked to parts of the coding sequences of any Bt insecticidal protein coding sequence to be expressed in a plant cell, so that it is effectively spliced in plant cells and a Bt insecticidal protein is produced. Effective splicing in plants cells can be measured using routine techniques, such as RT-PCR, Northern blotting, or the detection of a functional protein produced in plant cells. Of course, for effective splicing the intron needs to be inserted in the correct position of the coding sequence so that functional 5' and 3' splice sites are obtained in the sequence. The intron in the cry1C chimeric genes of the invention, such as in the cry1C1 or cry1C2 chimeric genes, is effectively spliced in rice plant cells, since high insect mortality is seen in insect bio-assays on plants expressing such cry1C chimeric genes. RT-PCR also shows that the plants comprising the cry1C gene of the invention produce an mRNA encoding the expected Cry protein.

In accordance with one embodiment of this invention, the Cry1C protein is targeted to intracellular organelles such as plastids, preferably chloroplasts, or mitochondria. For this purpose, the chimeric genes of the invention comprise a coding region encoding a signal or target peptide, linked to the DNA encoding the Cry1C protein of the invention. Particularly preferred peptides to be included in the proteins of this invention are the transit peptides for chloroplast or other plastid targeting, especially duplicated transit peptide regions from plant genes whose gene product is targeted to the plastids, such as the optimized transit peptide of SEQ ID No. 4, the optimized transit peptide described by Lebrun et al. (1996), or Capellades et al. (U.S. Pat. No. 5,635,618), the transit peptide of ferredoxin-NADP+oxidoreductase from spinach (Oelmuller et al., 1993), the transit peptide described in Wong et al. (1992) or the targeting peptides in published PCT patent application WO 00/26371. In one embodiment of the invention, the chloroplast transit peptide comprises the sequence of SEQ ID No. 4 from amino acid position 3 to amino acid position 124 or variant thereof, such as a chloroplast transit peptide comprising the sequence of SEQ ID No. 4 from amino acid position 3 to amino acid position 124, wherein the Cys amino acid at position 55 is replaced by Tyr in SEQ ID No. 4 and/or wherein a Gly amino acid is added after the Gly amino acid at position 51 in SEQ ID No. 4.

Particularly useful DNAs encoding signal peptides in accordance with the invention, to combine with a cry1C DNA of the invention, include the DNAs encoding any one of the following proteins, or combinations thereof: the chloroplast transit peptides described by Van Den Broeck et al. (1985), or the optimized chloroplast transit peptide of U.S. Pat. No. 5,510,471 and U.S. Pat. No. 5,635,618 causing transport of the protein to the chloroplasts, a secretory signal peptide or a peptide targeting the protein to other plastids, mitochondria, the ER, or another organelle. A preferred DNA encoding a transit peptide of the invention is a DNA comprising the sequence of SEQ ID No. 3 from nucleotide position 7 to nucleotide position 372, particularly the sequence of SEQ ID No. 3, or an equivalent sequence with at least 95%, particularly at least 97 or 99%, sequence identity to the sequence of SEQ ID No. 3 from nucleotide position 7 to nucleotide position 372.

Furthermore, for any target pest insect, the binding properties of the Cry proteins of the invention can be evaluated, using methods known in the art (e.g., Van Rie et al., 1990, EP 408-403), to determine if the Cry1 proteins of the invention bind to sites on a target insect midgut that are not recognized (or competed for) by other Cry or non-Cry proteins. Other Bt crystal proteins binding to different binding sites in relevant susceptible insects, or other toxins derived from Bt strains or other sources (such as VIP toxins (e.g., the VIP3A toxins listed at http://www.lifesci.sussex.ac.uk/home/Neil_Crickmore/Bt/vip.html, or the VIP3Aa toxin of Estruch et al., 1996) or insect (gut) proteinase inhibitors) with a different mode of action can be very valuable to also express in a plant in addition to any one of the cry1C genes of the invention, to prevent or delay the development of insect resistance to a plant expressing insecticidal toxins, and increase the spectrum of insects controlled by a plant of the invention. In one method, a protein having a different mode of action from the Cry1C protein of the invention can be found by screening proteins for their insecticidal effect on Cry1C-resistant insects, or alternatively when the biochemical mechanism or pathway by which such protein acts is found to be different from that used by the Cry1C protein, such that a mutation in the insect causing Cry1C resistance is unlikely to affect the toxicity of the other protein. Because of the characteristics of the new cry1C genes, they are extremely useful for transforming plants, e.g. monocot plants such as corn, sugarcane, rice or wheat and dicot plants such as cotton, soybean, eggplant and *Brassica* species plants, to protect these plants from insect damage.

Especially for insect resistance management purposes for a specific insect pest, it is preferred to combine a cry1C gene of this invention with another gene encoding a different insect control protein, particularly a Bt crystal protein. A preferred insect control protein to combine with the Cry1C proteins of this invention, particularly for simultaneous expression in plants, preferably rice plants, is a Cry1Ab protein. A "Cry1Ab protein", as used herein, is any insecticidal Cry1Ab protein, particularly an insecticidal protein comprising an amino acid sequence identical to or at least 95%, 97%, 98%, or 99% identical to the sequence of SEQ ID No. 12 from amino acid position 30 to amino acid position 617, or identical to or at least 95%, 97%, 98%, or 99% identical to the sequence of SEQ ID No. 12 from amino acid position 3 to amino acid position 617, or a insecticidal protein comprising an amino acid sequence identical to or at least 95%, 97%, 98%, or 99% identical to the sequence of SEQ ID No. 12 from amino acid position 3 to amino acid position 617 which is fused at its' N-terminus to the protein of SEQ ID No. 4.

In one embodiment, such co-expression is obtained by transforming a plant with a plasmid comprising a cry1C and cry1Ab chimeric gene, or by cotransforming a plant with a plasmid comprising a cry1C chimeric gene and a plasmid comprising a cry1Ab chimeric gene, or by transforming a plant already containing a chimeric cry1C gene of the invention, with a cry1Ab chimeric gene. A "cry1Ab chimeric gene", as used herein, is a chimeric gene encoding a Cry1Ab protein as defined above, e.g., a chimeric gene comprising the following operably-linked sequences: a) a coding region encoding an insecticidal Cry1Ab protein, comprising a DNA sequence with at least 95%, 97%, 98%, or 99% sequence identity to the DNA sequence of SEQ ID No. 11 from nucleotide position 88 to nucleotide position 1851, or comprising a DNA sequence with at least 95%, 97%, 98%, or 99% sequence identity to the DNA sequence of SEQ ID No. 11 from nucleotide position 7 to nucleotide position 1851, or comprising the DNA sequence of SEQ ID No. 11 from nucleotide position 88 to nucleotide position 1851, or comprising the DNA sequence of SEQ ID No. 11 from nucleotide position 7 to nucleotide position 1851, or comprising any of such DNA sequences, such as the sequence of SEQ ID No. 11 from nucleotide position 7 to nucleotide position 1851, linked at its 5 end to the transit peptide coding sequence of SEQ ID No. 3, and b) a (second) promoter region capable of directing expression in plant cells. The Cry1Ab protein encoded by such chimeric gene comprises an amino acid sequence at least 99% identical to the amino acid sequence of SEQ ID No. 12 from amino acid position 30 to amino acid position 617, or comprises an amino acid sequence at least 99% identical to the amino acid sequence of SEQ ID No. 12 from amino acid position 3 to amino acid position 617, or comprises an amino acid sequence at least 99% identical to the amino acid sequence of SEQ ID No. 12, or comprises the amino acid sequence of SEQ ID No. 12 from amino acid position 30 to amino acid position 617, or comprises the amino acid sequence of SEQ ID No. 12 from amino acid position 3 to amino acid position 617, or comprises the amino acid sequence of SEQ ID No. 12.

Transformed plants comprising both a co/1C and cry1Ab chimeric gene can also be obtained by crossing plants comprising any one of the chimeric cry1Ab genes as defined above, with plants comprising any one of the chimeric cry1C chimeric genes of the invention. In one embodiment, the plants, cells, seeds or grains of the invention, particularly the rice plants, cells, seeds or grains of the invention, comprise the chimeric cry1C gene of the invention and a chimeric cry1Ab gene, as defined above at the same genetic locus, so that these genes do not segregate in progeny plant cells, plants, seeds or grains.

General methods for obtaining expression of different Bt chimeric genes in the same plant in an effort to minimize or prevent resistance development to transgenic insect-resistant plants are described in EP patent 0 408 403.

For selection purposes but also for increasing the weed control options, the transgenic plants of the invention can also be transformed with a DNA encoding a protein inactivating a broad-spectrum herbicide or encoding a protein which is a variant of the protein target for the herbicide but which protein variant is insensitive to such herbicide, e.g., herbicides based on glufosinate or glyphosate. In case such herbicide resistance genes are later to be removed or crossed out of the cry1C plants of the invention, the herbicide resistance genes are preferably located at another locus than the cry1C or the cry1C and cry1Ab genes of the invention. A preferred herbicide resistance gene in accordance with this invention is a bar coding sequence (Thompson et al., 1987) operably-linked to a 35S promoter (Odell et al., 1985) and a 3' untranslated region of the nopaline synthase gene of *Agrobacterium* (Depicker et al., 1982) such that the plants transformed with such chimeric bar gene are resistant to glufosinate herbicides.

The insecticidally effective cry1C DNA of this invention, preferably the cry1C chimeric gene of this invention, can be stably inserted in a conventional manner into the nuclear genome of a plant cell, and the so-transformed plant cell can be used in a conventional manner to produce plants and seeds, comprising the cry1C gene of the invention, that are insect-resistant. In this regard, a disarmed Ti-plasmid, containing the insecticidally effective cry1C gene part, in *Agrobacterium*, e.g., *Agrobacterium tumefaciens*, can be used to transform the plant cell, and thereafter, a transformed plant can be regenerated from the transformed plant cell using any of known procedure, e.g., the procedures described in EP 0 116 718, EP 0 270 822, PCT publication WO 84/02913 and published European Patent application ("EP") 0 242 246 and in De Block et al. (1989). Preferred Ti-plasmid vectors each contain the insecticidally effective cry gene part between the border sequences, or at least located to the left of the right border sequence, of the T-DNA of the Ti-plasmid. Of course, other types of vectors can be used to transform the plant cell, using procedures such as direct gene transfer (as described, for example in EP 0 233 247), pollen mediated transformation (as described, for example in EP 0 270 356, PCT publication WO 85/01856, and U.S. Pat. No. 4,684,611), plant RNA virus-mediated transformation (as described, for example in EP 0 067 553 and U.S. Pat. No. 4,407,956), liposome-mediated transformation (as described, for example in U.S. Pat. No. 4,536,475), and other methods such as the methods for transforming certain lines of corn (e.g., U.S. Pat. No. 6,140,553; Fromm et al., 1990; Gordon-Kamm et al., 1990) and the method for transforming monocots generally (PCT publication WO 92/09696). For rice transformation, a preferred transformation method is described in WO 92/09696. For cotton transformation, especially preferred is the method described in PCT patent publication WO 00/71733. For soybean transformation, reference is made to methods known in the art, e.g., Hinchee et al. (1988) and Christou et al. (1990), or the method of WO 00/42207.

The resulting transformed plant can be used in a conventional plant breeding scheme to produce more transformed plants with the same characteristics or to introduce the insecticidally effective cry1C gene in other varieties of the same or related plant species. Seeds, which are obtained from the transformed plants, contain the insecticidally effective cry gene part as a stable genomic insert.

The insecticidally effective cry1C DNA of this invention, preferably a DNA comprising the sequence of SEQ ID No. 1 or 5, is inserted in a plant cell genome so that the inserted gene is downstream (i.e., 3') of, and under the control of, a promoter which can direct expression of the gene in a plant cell (herein named a "plant-expressible promoter"). This is preferably accomplished by inserting the cry1C chimeric gene comprising a plant-expressible promoter in the plant cell genome, particularly in the nuclear or plastid (e.g., chloroplast) genome. Preferred plant-expressible promoters include: the strong constitutive 35S promoters (the "356 promoters") of the cauliflower mosaic virus (CaMV) of isolates CM 1841 (Gardner et al., 1981), CabbB-S (Franck et al., 1980) and CabbB-JI (Hull and Howell, 1987); the 35S promoter described by Odell et al. (1985), promoters from the ubiquitin family (e.g., the maize ubiquitin promoter of Christensen et al., 1992, see also Cornejo et al., 1993), the gos2 promoter (de Pater et al., 1992), the emu promoter (Last et al., 1990), *Arabidopsis* actin promoters such as the promoter described by An et al. (1996), rice actin promoters such as the promoter described by Zhang et al. (1991) or McElroy et al. (1990); promoters of the Cassava vein mosaic virus (WO 97/48819, Verdaguer et al. (1998)), the pPLEX series of promoters from Subterranean Clover Stunt Virus (WO 96/06932), particularly the duplicated promoter region derived from the subterranean clover stunt virus genome segment 4 or 7 (referred to as the "S7S7" or "S4S4" promoters herein) described by Boevink et al. (1995) or Schünmann et al. (2003), an alcohol dehydrogenase promoter, e.g., pAdh1S (GenBank accession numbers X04049, X00581), and the TR1' promoter and the TR2' promoter (the "TR1' promoter" and "TR2' promoter", respectively) which drive the expression of the 1' and 2' genes, respectively, of the T-DNA (Velten et al., 1984). Alternatively, a promoter can be utilized which is not constitutive but rather is specific for one or more tissues or organs of the plant (e.g., leaves and/or roots) whereby the inserted cry gene part is expressed only in cells of the specific tissue(s) or organ(s). For example, the insecticidally effective cry gene part could be selectively expressed in the leaves of a plant (e.g., corn, cotton) by placing the insecticidally effective gene part under the control of a light-inducible promoter such as the promoter of the ribulose-1,5-bisphosphate carboxylase small subunit gene of the plant itself or of another plant such as pea as disclosed in U.S. Pat. No. 5,254,799. Another alternative is to use a promoter whose expression is inducible, preferably by wounding such as insect feeding, e.g., the MPI promoter described by Cordero et al. (1994, Genbank accession X78988), or the *Agrobacterium* TR2' or mannopine synthase promoter (Velten et al., 1984) or a promoter inducible by chemical factors. In one embodiment of the invention, if that is desired, expression of such wound-inducible promoters can be increased by placing a CaMV 35S promoter region or another promoter or at least a promoter enhancer element in the vicinity of, and preferably in the same direction (5' to 3') as, the wound-inducible promoter, so that basal expression levels are increased but induction upon wounding is retained.

In one embodiment of the invention, preferred promoters used in the cry1C chimeric gene of the invention or in the cry1Ab chimeric gene of the invention include promoters comprising the DNA sequence of any one of SEQ ID Nos. 9 (or comprising the sequence from nucleotide position 1 to 1997 in SEQ ID No. 9), 10, 13, 14, or an equivalent sequence differing in less than 1 to 5%, particularly less than 2%, of its nucleotides with any of such sequence. Such promoters can include an untranslated leader sequence, and can also comprise an intron. In one embodiment of the invention, the cry1C chimeric gene comprises the leader sequence of the *Zea mays* ubiquitin gene between the promoter and the coding region, e.g., as described by Christensen et al. (1992), and the cry1Ab chimeric gene comprises the intron and leader sequence of the rice Actin 1 gene (McElroy et al., 1990) between the promoter and the coding region.

The cry1C DNA is preferably inserted in the plant genome so that the inserted coding sequence is upstream (i.e., 5') of suitable 3' end transcription regulation signals (i.e., transcript formation and polyadenylation signals). This can be accomplished by inserting the cry1C chimeric gene in the plant cell genome. Preferred polyadenylation and transcript formation signals include those of the 3' untranslated region of the NADP-malic enzyme gene from *Flayeria bidentis* (Marshall et al., 1996), nopaline synthase gene (Depicker et al., 1982), the octopine synthase gene (Gielen et al., 1984) and the T-DNA gene 7 (Velten and Schell, 1985), which act as 3'-untranslated DNA sequences in transformed plant cells.

In one embodiment of this invention, the cry1C gene of the invention is transformed into plants selected from the group consisting of: corn, cotton, rice, soybean, sugarcane, wheat, canola, soybean, vegetable plants, Cruciferae plant species, *Brassica* plant species such as cauliflower, cabbage, Chinese cabbage, turnip, mustard, oilseed rape, kale, broccoli. In one embodiment of this invention the following *Brassica* species plants are protected from insects by the cry1C genes of this invention: *B. carinata, B. juncea, B. napus, B. nigra, B. oleracea*, and *B. rapa.*

The invention includes plants, cells or seeds, particularly rice plants, cells or seeds, transformed with a cry1C gene of the invention, as well as plants, cells or seeds, particularly rice plants, cells or seeds, containing the genes of the invention obtained after crossing or breeding with such transformed plants, cells or seeds. Such crossing or breeding can be done using traditional breeding techniques known in the art, but may also include known in vitro work such as doubled haploid production, embryo rescue, protoplast fusion, and the like. As such, the invention also relates to japonica rice plants, cells or seeds, and the progeny thereof that contain the cry1C gene of the invention, obtained from crossings with a cry1C-transformed indica rice plant, cell or seed, and to any uses of such plants, cells or seeds. Included herein are crosses of rice plants comprising any of the cry1C and/or cry1Ab chimeric genes of the invention with other plants comprising rice transformation events conferring insect control or another beneficial trait (e.g., herbicide tolerance, yield increase, stress tolerance, etc.), such as crosses with Bt-rice event TT51 expressing a Cry1Ab/Cry1Ac fusion protein (Chinese patent application 200510062980, publication number 1840655), or crosses with rice events expressing a Cry1Ca5 protein (such as event T1C-19, see Tang et al. 2006), a Cry1B protein (see, e.g., Breitler et al. (2001), or a Cry2A protein (see, e.g., Maqbool et al. (1998)), or expressing a Cry1Ab-Cry1B fusion protein (Ho et al., 2006), as well as rice plants comprising the stacked insect control genes or uses thereof to control insects, particularly rice stem borers or rice leaf folders.

Transformation of plant cells can also be used to produce the cry1C proteins of the invention in plant cell cultures, e.g., to produce a Cry1C protein that can then be applied onto crops after proper formulation. When reference to a transgenic plant cell is made herein, this refers to a plant cell (or also a plant protoplast) as such in isolation or in tissue culture, or to a plant cell (or protoplast) contained in a plant or in a differentiated organ or tissue, and both possibilities are specifically included herein. Hence, a reference to a plant cell in the description or claims is not meant to refer only to isolated cells in culture, but refers to any plant cell, wherever it may be located or in whatever type of plant tissue or organ it may be present. Plant cell, as used herein, also refers to protoplasts or pollen.

The coding sequence of the cry1C genes of the invention can also be used to transform microorganisms, such as a *B. thuringiensis* strain which has insecticidal activity against *Lepidoptera* or *Coleoptera*. Thereby, a transformed microorganism such as a Bt strain can be produced which is useful for combating a wide spectrum of lepidopteran and coleopteran insect pests or for combating additional lepidopteran insect pests. Transformation of microorganism, such as bacteria of the genus *Pseudomonas, Agrobacterium, Bacillus* or *Escherichia*, with the coding sequence of the cry1C genes of this invention, incorporated in a suitable cloning vehicle, can be carried out in a conventional manner, preferably using conventional electroporation techniques as described in Mahillon et al. (1989) and in PCT Patent publication WO 90/06999.

Transformed *Bacillus* species strains containing a cry1C coding sequence can be fermented by conventional methods (Dulmage, 1981; Bernhard and Utz, 1993) to provide high yields of cells. Under appropriate conditions which are well understood (Dulmage, 1981), these strains each sporulate to produce crystal proteins containing the Cry1C protein.

An insecticidal, particularly anti-lepidopteran, composition of this invention can be formulated in a conventional manner using the microorganisms expressing the Cry1C toxin as an active ingredient, together with suitable carriers, diluents, emulsifiers and/or dispersants (e.g., as described by Bernhard and Utz, 1993). This insecticide composition can be formulated as a wettable powder, pellets, granules or dust or as a liquid formulation with aqueous or non-aqueous solvents as a foam, gel, suspension, concentrate, etc.

A method for controlling insects, particularly *Lepidoptera*, preferably Lepidopteran rice insects such as stem borers and leaf folders, in accordance with this invention can comprise applying (e.g., spraying), to a locus (area) to be protected, an insecticidal amount of the Cry1C proteins or host cells transformed with the cry1C gene of this invention. The locus to be protected can include, for example, the habitat of the insect pests or growing vegetation, such as a rice field, or an area where vegetation is to be grown.

In one embodiment of this invention, insects against which the cry1C genes or Cry1C proteins of the invention can be used include insects selected from the group consisting of: *Plutella xylostella, Spodoptera exigua, Spodoptera littoralis, Spodoptera frugiperda, Trichoplusia ni Heliothis virescens, Mamestra brassicae, Pieris brassicae, Manduca sexta, Choristoneura fumiferana, Choristoneura occidentalis, Choristoneura rosaceana, Pandemis pyrusana, Platynota stultana, Lymantria dispar, Orgyia leucostigma, Malacosoma disstria, Lambina fiscellaria, Chilo suppressalis, Chilo plejadellus, Chilo polychrysa, Chilo partellus, Scirpophaga incertulas, Scirpophaga innotata, Sesamia* inferens, *Cnaphalocrocis medinalis, Marasmia patnalis, Argyrotaenia citrana, Artogeia rapa, Chrysomela scripta, Ostrinia nubilalis, Diatraea saccharalis, Pseudoplusia includens, Thaumetopoea pityocampa, Hereitogramma licarisalis, Naranga aenescens, Mycalesis gotama, Marasmia exigua, Marasmia ruralis, Nymphula depunctatis, Spodoptera litura, Rupela albinella, Spodoptera frugiperda, Mythimna unipuncta, Chilo zacconius* and *Parnara guttata.*

In one embodiment, preferred target insect pests are Lepidopteran rice insect pests such as rice stem borers or rice leaf folders, or Lepidopteran rice insect pests such as the striped stem borer *Chilo suppressalis*, the yellow stem borer *Scirpophaga incertulas* (also named *Tryporyza incertulas*), the white stem borer *Scirpophaga innotata* (also named *Tryporyza innotata*), the dark-headed stem borer *Chilo polychtysa*, the pink stem borer *Sesamia inferens*, the sugarcane borer *Diatraea saccharalis*, the rice stalk borer *Chin plejadellus*, the rice leaffolder *Marasmia patnalis*, the rice leaffolder *Cnaphalocrocis medinalis*, and insects such as *Hereitogramma licarisalis, Naranga aenescens, Mycalesis gotama, Marasmia exigua, Marasmia ruralis, Nymphula depunctalis, Spodoptera litura, Rupela albinella, Spodoptera frugiperda, Mythimna unipuncta, Chilo zacconius* and *Parnara guttata*. The proteins encoded by the cry1C or the cry1C and cry1Ab genes of this invention are particularly useful to control these insects, e.g., by expression of the cry1C and/or cry1Ab genes of the invention in cells of a plant, particularly in rice plant cells.

Such insects can be controlled by sowing, planting, or growing plants comprising any one of the cry1C chimeric genes of the invention in a field, or by securing the presence of a Cry1C protein of the invention in or on plants that can be infested by such insects (e.g., by sowing or planting a rice plant transformed with a cry1C chimeric gene of the invention, such as the cry1C1 or cry1C2 chimeric genes). The invention also relates to the use of the cry1C chimeric genes of this invention, at least the cry1C1 or cry1C2 chimeric genes, in plants, cells or seeds, particularly rice plants, cells or seeds, to protect them against Lepidopteran insect pests, preferably in combination with another cry gene, such as a cry1Ab chimeric gene, preferably the cry1Ab1 or cry1Ab2 chimeric genes.

In the current invention, also a modified coding sequence encoding an optimized chloroplast transit peptide is provided, as well as the use thereof to target a protein to the chloroplast. In one embodiment of the invention, the coding sequence for the optimized transit peptide comprises a nucleotide sequence identical to or with at least 95%, 97%, 98%, or 99% sequence identity to the nucleotide sequence of SEQ ID No. 3 from nucleotide position 7 to nucleotide position 372, particularly to the sequence of SEQ ID No. 3, or a DNA encoding a protein comprising an amino acid sequence identical to or with at least 95%, 97%, 98%, or 99% sequence identity to the sequence of SEQ ID No. 4. Also plant cells, plants or seeds, particularly rice plants cells, plants or seeds, comprising the modified transit peptide coding sequence of the invention, as well as the use of this transit peptide coding sequence for targeting any protein to the chloroplast, particularly to the chloroplast of rice plants, are included in this invention. In one embodiment of the invention, the coding sequence for the optimized transit peptide comprising the nucleotide sequence of SEQ ID No. 3 from nucleotide position 7 to nucleotide position 372, particularly the sequence of SEQ ID No. 3, is operably-linked to the DNA encoding a Cry1C protein of the invention, such as the cry1C1 or cry1C2 genes, and/or is operably linked to the coding sequence of the cry1Ab gene, such as the cry1Ab1 or cry1Ab2 coding sequences, so as to secure chloroplast targeting in the plant cells, plants or seeds of the invention, particularly rice plant cells, plants or seeds.

These and/or other embodiments of this invention are reflected in the wordings of the claims, that form part of the description of the invention.

The following Examples illustrate the invention, and are not provided to limit the invention or the protection sought. Unless otherwise stated, all recombinant DNA techniques are carried out according to standard protocols as described in Sambrook et al. (1989) Molecular Cloning: A Laboratory Manual, Second Edition, Cold Spring Harbour Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy published by BIOS Scientific Publications Ltd (UK) and Blackwell Scientific Publications, UK.

The enclosed sequence listing referred to in the Examples, the Claims and the Description is as follows:

SEQUENCE LISTING

SEQ ID No. 1: cry1C1 DNA sequence, optimized for expression in plants
SEQ ID No. 2: amino acid sequence of the Cry1C1 protein encoded by SEQ ID No. 1
SEQ ID No. 3: coding sequence encoding an optimized chloroplast transit peptide
SEQ ID No. 4: amino acid sequence of the chloroplast transit peptide encoded by the sequence of SEQ ID No. 3
SEQ ID No. 5: optimized cry1C1 DNA sequence operably-linked to the sequence of SEQ ID No. 3, encoding the Cry1C2 protein
SEQ ID No. 6: amino acid sequence of the Cry1C2 protein encoded by SEQ ID No. 5
SEQ ID No. 7: cry1C primer P1C203
SEQ ID No. 8: cry1C primer P1C204
SEQ ID No. 9: *Zea mays* ubiquitin promoter, including the *Zea mays* ubiquitin 5' untranslated leader and intron sequence (pUbi)
SEQ ID No. 10: *Zea mays* protease inhibitor (mpi(2K)) promoter (pMPI(2K))
SEQ ID No. 11: optimized cry1Ab coding sequence
SEQ ID No. 12: amino acid sequence of the Cry1Ab protein encoded by the sequence of SEQ ID No. 11
SEQ ID No. 13: *Oryza sativa* Actin 1 promoter comprising intron sequence (pAct1)
SEQ ID No. 14: *Zea mays* protease inhibitor (mpi(C1)) promoter (pMPI(C1))

EXAMPLES

1. Construction of Chimeric Genes and Transformation Vectors

Several cry1C chimeric genes for transformation of plants, particularly rice plants, were designed. The use of a diversity of genes and regulatory elements allows the selection of plants for different purposes or uses. Bioassays with the Cry1C protein of SEQ ID No. 2 (Cry1Ca4) show that this protein is toxic to the Lepidopteran insects *Scirpophaga incertulas, Sesamia inferens, Spodoptera litura, Spodoptera exigua, Marasmia patnalis*, and *Cnaphalocrocis medinalis*, and hence is a useful protein to express in transgenic plants.

The cry1C DNA which was designed for optimal expression in plant cells, particularly rice, is represented in SEQ ID No. 1. This cry1C1 DNA has the corn Adh1 intron I (Dennis et al., 1984) inserted into the cry1C coding sequence. This DNA encodes the insecticidal Cry1C1 protein of the invention (SEQ ID No. 2). For transformation of plants, several chimeric genes were constructed (the cry1C1 chimeric genes) comprising the following operably-linked elements (5' to 3'): a promoter comprising the promoter region of SEQ ID No. 9 (pUbi) or 10 (pMPI(2K)), the cry1C1 DNA of SEQ ID No. 1, and the sequence including the 3' untranslated region of the octopine synthase gene from *Agrobacterium* (De Greve et al., 1983).

To secure targeting of the Cry1C protein to the plant cell chloroplast, also a variant of the cry1C1 chimeric gene was constructed which comprises a modified sequence encoding an optimized transit peptide (SEQ ID No. 4) essentially as described by Lebrun et al. (1996), operably-linked to the DNA encoding the Cry1C1 protein so that a transit peptide fusion protein (the Cry1C2 protein) is expressed in plant cells. For transformation of plants, several chimeric genes were constructed (the cry1C2 chimeric genes) comprising the following operably-linked elements (5' to 3'): a promoter comprising the promoter region of SEQ ID No. 9 or 10, the cry1C2 DNA of SEQ ID No. 5, and the sequence including the 3' untranslated region of the octopine synthase gene from *Agrobacterium* (De Greve et al., 1983).

To obtain plants expressing two different Cry proteins, also cry1Ab chimeric genes were designed and assembled to achieve a set of cry1Ab chimeric genes to be used in plants, particularly rice plants. Also here different genes and regulatory elements were used to allow the selection of plants for different purposes or uses.

The cry1Ab1 DNA which was designed for optimal expression in plant cells is represented in SEQ ID No. 11. This DNA encodes the insecticidal Cry1Ab1 protein (SEQ ID No. 12). For transformation of plants, several chimeric genes are constructed (the cry1Ab1 chimeric genes) comprising the following operably-linked elements (5' to 3'): a promoter comprising the promoter region of SEQ ID No. 9, 10, 13 or 14, the cry1Ab1 DNA of SEQ ID No. 11, and the sequence including the 3' polyadenylation and transcript termination region of the octopine synthase gene from *Agrobacterium* (De Greve et al., 1983).

To secure targeting of the Cry1Ab protein to the plant cell chloroplast, a variant of the cry1Ab1 chimeric gene is constructed which comprises a modified sequence encoding an optimized transit peptide (SEQ ID No. 4) essentially as described by Lebrun et al. (1996), operably-linked to the cry1Ab1 coding region so that a transit peptide fusion protein (the Cry1Ab2 protein) is expressed in plant cells. For transformation of plants, several chimeric genes are constructed (the cry1Ab2 chimeric genes) comprising the following operably-linked elements (5' to 3'): a promoter comprising the promoter region of SEQ ID No. 9, 10, 13 or 14, the transit peptide DNA of SEQ ID No. 3 linked upstream (5') of the cry1Ab1 DNA of SEQ ID No. 5 from nucleotide position 7 to nucleotide position 1854, and the sequence including the 3' untranslated region of the octopine synthase gene from *Agrobacterium* (De Greve et al., 1983).

In some chimeric genes, also a CaMV 35S promoter region is used to control transcription of the operably-linked cry1C(1 or 2) or cry1Ab(1 or 2) coding sequences described above.

The transformation vectors (intermediate cloning vectors) containing the genes of the invention were derived from pGSC1700 (Cornelissen and Vandewiele, 1989). The vector backbone contains the following genetic elements:

a) the plasmid core comprising the origin of replication from the plasmid pBR322 (Bolivar et al., 1977) for replication in *Escherichia coli* and a restriction fragment comprising the origin of replication from the *Pseudomonas* plasmid pVS1 (Itoh et al., 1984) for replication in *Agrobacterium tumefaciens*.

b) a selectable marker gene conferring resistance to streptomycin and spectinomycin (aadA) for propagation and selection of the plasmid in *Escherichia coli* and *Agrobacterium tumefaciens*.

c) a DNA region consisting of a fragment of the neomycin phosphotransferase coding sequence of the nptl gene from transposon Tn903 (Oka et al., 1981).

The T-DNA region of each transformation vector can also further contain—besides one of the above cry genes—a chimeric bar gene that serves as selectable marker gene. Expression of the bar gene enables the production of an enzyme, phosphinothricin-acetyl transferase, that metabolizes the herbicide glufosinate-ammonium, thus rendering it non-herbicidal in the plant. The chimeric bar gene comprises the 35S3 promoter region from the Cauliflower Mosaic Virus 35S transcript (Odell et al., 1985), the bar coding sequence of the phosphinothricin acetyltransferase gene of *Streptomyces hygroscopicus* as described by Thompson et al. (1987), and a 3' transcript termination and polyadenylation sequence from the 3' untranslated region of the nopaline synthase gene from the T-DNA of pTiT37 (Depicker et al., 1982). In some transformations, two intermediate cloning plasmids are used for transformation: one plasmid containing the cry1C chimeric gene or containing both the cry1C and cry1Ab chimeric genes, the other plasmid containing the chimeric bar gene; in other transformations one plasmid comprises the cry1C chimeric gene and another plasmid comprises the cry1Ab chimeric gene (one of each or both such plasmids can also comprise a chimeric bar gene). This approach allows obtaining different types of rice transformants with the different genes at different loci or at the same locus in the genome of the rice plants, so that in some plants one chimeric gene (e.g., the bar gene, or one of the cry genes) can be removed from the other chimeric gene(s) in the plants by breeding, e.g., in case herbicide tolerance in the final rice plants to be marketed is not required, or in case only the cry1C gene is to be crossed into rice plants containing another cry gene (such as a stack of the cry1C gene of the invention with the cry1A gene in rice event TT51 (Chinese patent application 200510062980, publication number 1840655)).

All constructed plasmids are confirmed to be accurate by restriction enzyme digest analysis and by DNA sequencing, before they are used for plant transformation.

2. Plant Transformation and Regeneration

The acceptor *Agrobacterium* strain carries a non-oncogenic (disarmed) Ti plasmid from which the T-region has been deleted. This Ti plasmid carries the necessary vir gene functions that are required for transfer of the T-DNA region (containing the above cry1C and/or cry1Ab chimeric genes) of the intermediate cloning vector to the plant genome. It also has a homology region that allows cointegrate formation with the intermediate cloning vector.

The intermediate cloning vector is constructed in *Escherichia coli*. It is transferred to the acceptor *Agrobacterium tumefaciens* strain via a triparental mating involving an *E. coli* strain that carries a mobilization helper plasmid. The structure of the T-DNA in the resulting *Agrobacterium* strain is confirmed by Southern blot hybridization (Deblaere et al., 1985).

*Agrobacterium*-mediated gene transfer of the intermediate cloning vector(s) results in transfer of the DNA fragment between the T-DNA border repeats to the plant genome.

As target tissue for transformation, immature embryo or embryo-derived callus derived from japonica and indica rice cultivars was used which has been cut into small pieces, essentially using the technique described in PCT patent publication WO 92/09696.

*Agrobacterium* was co-cultivated with the rice tissues for some days, and then removed by suitable antibiotics. Transformed rice cells were selected by addition of glufosinate ammonium (with phosphinothricin 5 mg/L) to the rice tissue culture medium.

Calli growing on media with glufosinate ammonium were transferred to regeneration medium. When plantlets with roots and shoots develop, they were transferred to soil, and placed in the greenhouse.

When they flower, selected transformed rice plants were self-pollinated, and seeds comprising the introduced chimeric genes were harvested when mature.

Oilseed rape plants are also transformed with the cry1C and/or cry1Ab chimeric genes of the invention using *Agrobacterium tumefaciens*. Hypocotyl explants of *Brassica napus* are used in routine transformation and regeneration methods, e.g., the method described by De Block et al. (1989).

3. Analysis of Transformants

Once the transformed rice plants were regenerated, PCR and Southern analysis are used to confirm integration of the transgenes. Specific primers for detecting the presence of the cry1C coding region of the invention were prepared, they were designated PS1203 and P1C204 (SEQ ID No. 7 and 8, respectively).

Rice and oilseed rape plants having a single copy of the cry1C chimeric gene integrated into their genome are selected by means of Southern blot. Immunological analysis such as Cry1C (or Cry1Ab-)-specific ELISA assays or Western blots are used to select those transformed plants showing optimal expression levels of the Cry1C protein or of the Cry1C and Cry1Ab protein. Initial ELISA assays on 12 T0 plants comprising different transformation events obtained after transforming rice plants with a plasmid comprising the PUbi-cry1C1-3' ocs chimeric gene (besides a P35S-bar-3' nos chimeric gene and a PAct1-cry1Ab1-3' ocs chimeric gene) showed values of the Cry1Ca4 protein ranging between 8.4 and 47.9 microgram/gram fresh leaf weight, confirming good expression of the Cry1Ca protein in these transformed rice plants.

RT-PCR experiments on RNA collected from rice plants shown to be transformed with the cry1C genes of SEQ ID No. 1 or 3, comprising a plant intron, showed that splicing occurs correctly and that a functional Cry1C protein is produced.

Insect assays using *Spodoptera exigua* neonate larvae under standard insect bio-assay conditions on selected transformed rice plants containing the cry1C2 gene of the invention under control of the mpi promoter of SEQ ID No. 10 (pMPI), showed that the transformed plants have high insecticidal activity. After 3 days, in all rice plants showing significant expression of the Cry1C protein in ELISA assays, 100% mortality was found for the *S. exigua* larvae, with some plants showing no visible leaf damage, while the control plants or plants without detectable expression levels of Cry1C, showed severe leaf damage or had no remaining leaves. These insect assays confirm that the intron contained in the coding region of the cry1C2 chimeric gene of the invention is correctly spliced in the transgenic rice plants.

Effective splicing in oilseed rape plants is seen in the clear insecticidal effects in insect bio-assays on plants transformed with the cry1C chimeric genes of the invention.

Also, in the rice plants expressing a Cry1C or Cry1Ab protein under control of a MPI promoter, a significant increase in expression of the Cry1C or Cry1Ab protein has been demonstrated in the plants that were wounded.

Initial greenhouse trials with single gene-copy cry1C, cry1Ab, and cry1C+cry1Ab-transformed rice plants (representing a variety of different transformation events where the chimeric genes were under the control of the above-described pMPI(2K) or pUbi, some chimeric genes containing the transit peptide of SEQ ID No. 4 operably-linked to the cry coding region (see enclosed Table 1)) using pink stem borer (*Sesamia inferens*) insect infestation (60 larvae/plant applied at different dates) confirmed the high insecticidal activity of both the single gene and dual gene rice plants (T1 plants, 10 plants analyzed per transformation event). While in untransformed control rice plants there was a high number of "dead heart", the number of tillers per plant was low (about 6 per plant), the complete leaf sheath was damaged, and larger insect larvae or pupa were found on the plants; in the transformed Cry1C, Cry1Ab and in the dual Bt (Cry1C+Cry1Ab) rice plants, no dead hart was seen, the number of tillers per plant was higher (between about 7 to about 13 tillers per plant, most above 10 tillers per plant), no or only some insect entry holes were found while the leaf sheath was not showing any major damage, and no live insects were found on most plants. Most transgenic rice plants showed an absence of insect tunnels, while the stem of the control plants was completely tunneled. ELISA assays confirm that these plants have significant and clearly detectable levels of Cry1C and Cry1Ab protein.

An excerpt of the initial insect assay data after pink stem borer infestation (for selected rice transformation events) are shown in Table 1 enclosed below, which shows the average values for the data obtained from 10 plants per transformation event.

Initial greenhouse trials for yellow stem borer (*Scirpophaga incertulas*) also showed good resistance of transgenic T1 plants (2 plants per event were tested, events were transformed with the same chimeric gene(s) as mentioned in column 1 of Table 1) to this insect (10-15 larvae were applied per plant). For this insect, no live larvae were found (about one month after insects were applied) on the rice plants containing the chimeric cry genes, while in the untransformed control plants several later instar larvae and pupae were found (also after about one month). None of the rice plants containing the chimeric cry genes of the invention (cry1C, cry1Ab or cry1C+cry1Ab) showed symptoms of dead heart, or showed any tunnels, while control plants were heavily damaged (high level of dead hearth and many tunnels).

Further selection of transformed rice plants expressing the Cry1C protein, or expressing the Cry1C and Cry1Ab proteins, is done using insect tests on yellow stem borer, pink stem borer and leaf folders in the greenhouse. For these tests, several transgenic plant series of each preselected transformation event (as well as negative controls) are grown in a greenhouse and infested with neonate larvae of either the yellow stem borer, the pink stem borer or the rice leaffolder at different stages of rice development.

Plants of a first series are infested with neonate larvae of the yellow stem borer, the pink stem borer or rice leaffolder, at the tillering stage. About three weeks later all plants are dissected and scored for insect damage for each insect tested (for percentage dead hart and larval survival for the yellow stem and pink stem borer, and for percentage damaged tillers, larval survival, and damage rating (0-9) for rice leaffolder).

A second series of plants is infested with neonate larvae of the yellow stem borer, or the pink stem borer, at the heading stage. About three weeks later all plants are dissected and scored for insect damage (for percentage white head and larval survival).

A third series of plants is infested with neonate larvae of the yellow stem borer or the pink stem borer, at the post flowering stage. About three weeks later all plants are dissected and scored for insect damage (for percentage white head and larval survival).

The oilseed rape and rice plants showing optimal insect control are selected for further analysis and reproduction.

Progeny plants and seeds are also obtained from the transformed, selected plants of the invention, and the genes of the invention are shown to segregate in such progeny in the expected Mendelian fashion. Selection of the transgenic plants in the greenhouse and in the field at multiple locations results in the identification of plant lines which have optimal stability and expression of the cry1C (or cry1C and cry1Ab) chimeric genes combined with optimal agronomical performance. Crossing of the selected best performing transgenic events into different commercial germplasm, after repeated backcrossing, results in the presence of the cry1C gene of the invention, or the cry1C and cry1Ab genes in different genetic backgrounds, optimally adapted to different areas or climatic conditions.

CITED REFERENCES

An et al. (1996) Plant J. 10, 107

Bernhard and Utz (1993) "Production of *Bacillus thuringiensis* insecticides for experimental and commercial uses", In *Bacillus thuringiensis*, An Environmental Biopesticide Theory and Practice, pp. 255-267, eds. Entwistle, P. F., Cory, J. S., Bailey, M. J. and Higgs, S., John Wiley and Sons, New York (1993).

Boevink et al. (1995) Virology, 207, 354-361.

Bolivar et al. (1977) Gene, 2: 95-113.

Bradford et al. (1976) Anal. Biochem. 72, 248-254.

Breitler et al. (2001) Molecular Breeding 7, 259-274.

Brown (1986) Nucleic Acids Res. 1986 14, 9549-9559.

Brown and Simpson (1998) Ann. Rev. Plant Physiol. Plant Mol. Biol. 49, 77-95.

Brown et al. (1996) Plant Mol. Biol. 32, 531-535.

Cao et al. (1999) Molecular breeding 5, 131-141.

Cheng et al. (1998) Proc Natl Acad Sci USA 95, 2767-2772.

Christensen et al. (1992) Plant Mol. Biol. 18, 675-689.

Christou et al. (1990). Trends Biotechnology 8, 145.

Cordero et al. (1994) The Plant Journal 6, 141.

Cornejo et al. (1993) Plant Mol. Biol. 23, 567-581.

Cornelissen & Vandewiele (1989) Nucleic Acids Research, 17: 19-25.

Crickmore et al. (1998) Microbiol. Mol. Biol. Rev. 62(3), 807-13.

Crickmore et al. (2005) "*Bacillus thuringiensis* toxin nomenclature", kept and updated at: http://www.lifesci.sussex.ac.uk/HomeNeil_Crickmore/Bt/

Deblaere et al. (1985) Nucl. Acids Res. 13, 4777-4788.

De Block et al. (1989) Plant Physiol., 91: 694.

De Greve et al. (1983) J. Mol. Appl. Genet. 1(6), 499-511.

Dennis et al. (1984) Nucleic Acids Res. 12(9): 3983-4000.

De Pater et al., 1992, Plant J. 2, 834-844.
Depicker et al. (1982) Journal of Molecular and Applied Genetics, 1: 561-573.
Duan et al. (1996) Nature Bio/Technology 14, 494-498.
Dulmage (1981), "Production of Bacteria for Biological Control of Insects" in Biological Control in Crop Production, Ed. Paparizas, D. C., Osmun Publishers, Totowa, N.J., USA, pp. 129-141 (1981).
Eckes et al. (1986) Molecular and General Genetics, 205: 14-22.
Estruch et al., (1996), Proc Natl Acad Sci USA 93, 5389-94.
Ffrench-Constant and Bowen (2000) Cell Mol Life Sci 57, 828-33.
Franck et al. (1980) Cell 21, 285-294.
Fromm et al. (1990) Bio/Technology 8, 833-839.
Fujimoto et al. (1993) Biotechnology 11(10), 1151-1155.
Gardner et al. (1981) Nucleic Acids Research 9, 2871-2887.
Ghareyazie et al. (1997) Molecular Breeding 3, 401-414.
Gielen et al. (1984) EMBO J. 3, 835-845.
Gordon-Kamm et al. (1990) The Plant Cell 2, 603-618.
Heinrichs (1994) pp. 3-11 in Biology and management of rice insects, Wiley Eastern Limited and New Age International Limited, ed. E. A. Heinrich
Hinchee et al. (1988) Bio/Technology 6, 915.
Ho et al. (2006) Crop Science 46, 781-789.
Höfte et al. (1988) Appl. and Environm. Microbiol. 54, 2010-2017.
Hull and Howell (1987) Virology 86, 482-493.
Itoh et al. (1984) Plasmid, 11: 206-220.
Jansens et al. (1997) Crop Science 37, 1616-1624.
Karim et al. (1997) General Meeting of the International Program on Rice Biotechnology of the Rockefeller Foundation, Annual Progress Meeting 15-19 Sep. 1997, Malacca, Malaysia, p. 241.
Last et al. (1990) Theor. Appl. Genet. 81, 581-588.
Lebrun et al. (1996) U.S. Pat. No. 5,510,471.
Lee et al. (1997) General Meeting of the International Program on Rice Biotechnology of the Rockefeller Foundation, Annual Progress Meeting 15-19 Sep. 1997, Malacca, Malaysia, p. 343.
Mahillon et al, FEMS Microbiol. Letters 60, 205-210 (1989).
Marshall et al. (1996) Plant Physiology, 111: 1251-1261.
Maqbool et al. (1998) Molecular Breeding 4, 501-507.
McElroy et al. (1990) Plant Cell 2, 163-171.
Nayak et al. (1997) Proc. Natl. Acad. Sci. USA 94, 2111-2116.
Needleman and Wunsch (1970) J. Mol. Biol., 48: 443-53.
Odell et al. (1985) Nature, 313: 810-812.
Oelmuller et al., Mol. Gen. Genet. 237, 261-272 (1993).
Oka et al. (1981) Journal of Molecular Biology, 147: 217-226.
Rao et al. (1998) Plant J. 15(4), 469-477.
Rice et al. (2000) Trends in Genetics, 16: 276-277.
Schünmann et al. (2003) Functional Plant Biology 30, 453-460.
Shcherban et al. (1995) Proc. Natl. Acad. Sci. USA 92, 9245-9249.
Stanssens et al. (1989), Nucleic Acids Research 12, 4441-4454.
Strizhov et al. (1996) Proc. Natl. Acad. Sci. 93:15012-15017.
Strizhov et al. (1998) PCT patent publication WO 98/15630.
Tang et al. (2006) Molecular Breeding 18, 1-10.
Thompson et al. (1987) The EMBO Journal, 6: 2519-2523.
Van Den Broeck et al., 1985, Nature 313, 358.
Van Rie et al. (1990) Science 247, 72.
Velten et al. (1984) J., EMBO J. 3, 2723-2730.
Velten and Schell (1985) Nucleic Acids Research 13, 6981-6998.
Verdaguer et al. (1998) Plant Mol. Biol. 37, 1055-1067.
Waterfield et al. (2001) Trends Microbiol 9, 185-91.
White et al. (1989) Trends in Genet. 5, 185-189.
Wong et al. (1992) Plant Molec. Biol. 20, 81-93.
Wu et al. (1997). Plant Cell Reports 17, 129-132.
Wunn et al. (1996) Biotechnology 14(2), 171-176.
Xu et al. (1996) Molecular Breeding 2, 167-173.
Zhang at al. (1991) The Plant Cell 3, 1155-1165.
Zhao et al. (2003) Nature Biotechnology, 21: 1493-1497.

All cited references are hereby incorporated by reference into the description. The citation of any of these references is not to be construed as an acknowledgement of the accuracy of every statement contained in such reference, nor as an acknowledgement that such reference is relevant prior art, has a sufficient (or enabling) disclosure, or forms part of the common general knowledge in any country.

TABLE 1 average data of pink stem borer insect assays on selected rice transformation events comprising chimeric cry genes

| Chimeric cry gene(s) | Dead hart | Tillers per plant | Entry Holes (1st leaf sheath) | Entry Holes (2st leaf sheath) | Insects/plant | Tunnels |
|---|---|---|---|---|---|---|
| pMPI(2k)-cry1Ab1-3'ocs | 0 | 10.3 | 5.7 | 0.6 | 0 | |
| pUbi-cry1Ab1-3'ocs | 0 | 10 | 6.5 | 0 | 0 | |
| pMPI(2k)-cry1Ab2-3'ocs | 0 | 12.2 | 6.6 | 0.1 | 0 | |
| pMPI(2k)-cry1C1-3'ocs | 0 | 11.1 | 3.9 | 0 | 0 | |
| pMPI(2k)-cry1C2-3'ocs | 0 | 11.3 | 7.7 | 0 | 0 | |
| pUbi-cry1C1-3'ocs | 0 | 12.7 | 8 | 0 | 0 | |
| pUbi-cry1C2-3'ocs | 0 | 9.4 | 3 | 0 | 0 | |
| pMPI(2k)-cry1Ab1-3'ocs + pMPI(2k)-cry1C1-3'ocs | 0 | 10.7 | 7.6 | 0.1 | 0 | 1 plant, 1 cm tunnel |
| pMPI(2k)-cry1Ab2-3'ocs + pMPI(2k)-cry1C2-3'ocs | 0 | 10 | 8.6 | 0.2 | 0.1 (4th instar) | 1 plant, 5 cm and 1 plant 2 cm tunnel |
| pMPI(2k)-cry1Ab2-3'ocs + pMPI(2k)-cry1C2-3'ocs | 0 | 13.4 | 6.5 | 0 | 0 | |
| pUbi-cry1C1-3'ocs + pUbi-cry1Ab1-3'ocs | 0 | 11 | 9.6 | 0.2 | 0 | |

TABLE 1-continued average data of pink stem borer insect assays on selected rice transformation events comprising chimeric cry genes

| Chimeric cry gene(s) | Dead hart | Tillers per plant | Entry Holes (1st leaf sheath) | Entry Holes (2st leaf sheath) | Insects/plant | Tunnels |
|---|---|---|---|---|---|---|
| pUbi-cry1C2-3'ocs + pUbi-cry1Ab2-3'ocs | 0.1 | 11.8 | 12.7 | 0.4 | 0 | 1 plant, 2 cm tunnel |
| control 1 | 5.9 | 5.9 | complete leaf sheath damaged | complete leaf sheath damaged | 2, 6; many escaped 4th/5th instar and some pupae | 100% tunnels |
| control 2 | 6.7 | 6.7 | complete leaf sheath damaged | complete leaf sheath damaged | 2, 8; many escaped 4th/5th instar and some pupae | 100% tunnels |
| control 3 | 6.2 | 6.2 | complete leaf sheath damaged | complete leaf sheath damaged | 2; many escaped 4th/5th instar and some pupae | 100% tunnels |

The invention claimed is:

1. A chimeric gene, comprising the following operably-linked sequences:

(a) a promoter region capable of directing expression in plant cells;

(b) a DNA encoding an insecticidal Cry1 C protein, comprising a DNA sequence with at least 99% sequence identity to the DNA sequence of SEQ ID No. 1 from nucleotide position 82 to nucleotide position 2415, or to the DNA sequence of SEQ ID No. 5 from nucleotide position 7 to nucleotide position 2784; and (c) a 3' polyadenylation and transcript termination region, wherein said Cry1C protein comprises a sequence with at least 99% sequence identity to the amino acid sequence from the amino acid at position 28 to the amino acid at position 627 in SEQ ID No. 2, and wherein said Cry1C protein contains a Glu amino acid at position 124 in SEQ ID No. 2.

2. The chimeric gene of claim 1, wherein said insecticidal Cry1C protein comprises the amino acid sequence of SEQ ID No. 2 from amino acid position 28 to amino acid position 627, or comprises the amino acid sequence of SEQ ID No. 6 from amino acid position 3 to amino acid position 750.

3. The chimeric gene of claim 1, wherein said DNA encoding an insecticidal Cry1 C protein comprises the DNA sequence of SEQ ID No. 1 from nucleotide position 82 to nucleotide position 2415, the DNA sequence of SEQ ID No. 5 from nucleotide position 7 to nucleotide position 2784, or comprises SEQ ID No. 1 or SEQ ID No. 5.

4. The chimeric gene of claim 1, wherein said insecticidal Cry1 C protein comprises the amino acid sequence of SEQ ID No. 2 or SEQ ID No. 6.

5. The chimeric gene of claim 1, wherein said promoter region comprises the sequence of any one of SEQ ID No. 9, 10, 13 or 14.

6. The chimeric gene of claim 1, wherein said 3' polyadenylation and transcript termination region is from the octopine synthase gene of *Agrobacterium tumefaciens*.

7. An isolated DNA comprising the chimeric gene of claim 1 and further comprising a second chimeric gene, wherein said second chimeric gene comprises the following operably-linked sequences:
(a) a second promoter region capable of directing expression in plant cells,
(b) a second coding region encoding an insecticidal Cry1Ab protein, comprising a DNA sequence with at least 95% sequence identity to the DNA sequence of SEQ ID No. 11 from nucleotide position 88 to nucleotide position 1851, and
(c) a 3' polyadenylation and transcript termination region, wherein said Cry1Ab protein comprises a sequence with at least 99% sequence identity to the amino acid sequence of SEQ ID No. 12 from amino acid position 30 to amino acid position 617.

8. The DNA of claim 7, comprising as second coding region a DNA sequence with at least 95% sequence identity to the DNA sequence of SEQ ID No. 11 from nucleotide position 7 to nucleotide position 1851, linked downstream (3') of the transit peptide coding sequence of SEQ ID No. 3 so that a fused coding region encoding a fusion protein is produced.

9. The DNA of claim 7, wherein said Cry1Ab protein comprises an amino acid sequence with at least 99% sequence identity to the sequence of SEQ ID No 12 from amino acid position 3 to amino acid position 617, or to the sequence of SEQ ID No. 1.

10. The DNA of claim 7, wherein said second promoter region is different from the Cry1C chimeric gene promoter region, and comprises the sequence of any one of SEQ ID No 9, 10, 13 or 14.

11. A transgenic plant cell comprising the chimeric gene of claim 1, wherein said chimeric gene is stably incorporated in its genome.

12. A transgenic plant cell comprising the chimeric gene of claim 1, and a second chimeric gene comprising the following operably-linked sequences:
(a) a second promoter region capable of directing expression in plant cells,
(b) a second coding region encoding an insecticidal Cry1Ab protein, comprising a DNA sequence with at least 95% sequence identity to the DNA sequence of SEQ ID No 11 from nucleotide position 88 to nucleotide position 1851, or at least 95% sequence identity to the DNA sequence of SEQ ID No. 11 from nucleotide position 7 to nucleotide position 1851, or at least 95% sequence identity to the DNA sequence of SEQ ID No. 11, and
(c) a second 3' polyadenylation and transcript termination region, wherein said Cry1Ab protein comprises a sequence with at least 99% sequence identity to the amino acid sequence of SEQ ID No. 12 from amino acid position 30 to amino acid position 617.

13. The plant cell of claim 12, comprising as second coding region a DNA sequence with at least 95% sequence identity to the DNA sequence foamed of SEQ ID No. 11 from nucleotide position 7 to nucleotide position 1851, linked downstream (3') of the transit peptide coding sequence of SEQ ID No. 3 so that a fused coding region encoding a fusion protein is produced.

14. The plant cell of claim 12, wherein said Cry1Ab protein comprises an amino acid sequence with at least 99% sequence identity to the sequence of SEQ ID No. 12 from amino acid position 3 to amino acid position 617, or to the sequence of SEQ ID No. 12.

15. The plant cell of claim 12, wherein said second promoter region is different from the cry1C chimeric gene promoter region, and comprises the sequence of any one of SEQ ID No. 9, 10, 13 or 14.

16. A plant or seed comprising the plant cell of claim 11.

17. The plant cell of claim 16, wherein said cells are rice plant cells.

18. A rice plant comprising the plant cells of claim 17.

19. The plant or seed of claim 16 wherein said plant or seed is corn, cotton, soybean, sugarcane, wheat, oilseed rape, soybean, cauliflower, cabbage, Chinese cabbage, turnip, mustard, oilseed rape, kale, or broccoli.

20. Seed, grain, or processed grain from the rice plant of claim 18.

21. The processed grain of claim 20, wherein said grain is milled, polished, dehusked, parboiled, converted, broken, steamed, or cooked grain, so that it no longer contains a viable embryo that can grow into a plant.

22. A rice plant resistant to Lepidopteran rice stem borers or rice leaf folders, comprising stably integrated in its genome, the chimeric gene of claim 1.

23. The rice plant of claim 22, wherein said rice plant is resistant to *Chilo suppressalis, Marasmia patnalis, Scirpophaga incertulas* or *Cnaphalocrocis medinalis.*

24. A method for controlling Lepidopteran plant insect pests, comprising: planting or sowing in a field, plants comprising the chimeric gene of claim 1.

25. A method for controlling Lepidopteran plant insect pests, comprising: expressing the chimeric genes of claim 1.

26. The method of claim 24, wherein said Lepidopteran plant insect pests are rice stem borers or rice leaf folders.

27. A process for obtaining a rice plant and progeny thereof resistant to *Chilo suppressalis, Marasmia patnalis, Cnaphalocrocis medinalis*, or *Scirpophaga incertulas*, comprising transforming a rice plant with the chimeric gene of claim 1.

28. A method of producing plants or seeds resistant to insects, comprising the steps of:
(a) obtaining a plant transformed with the gene of claim 1, and
(b) selecting progeny of said plant, or seeds thereof containing said gene, using specific primers or probes.

29. A microorganism comprising the chimeric gene of claim 1.

30. The microorganism of claim 29, which is of the genus *Escherichia, Bacillus* or *Agrobacterium.*

31. A transgenic plant cell comprising the DNA of claim 7, wherein said DNA is stably incorporated in its genome.

32. A rice plant resistant to Lepidopteran rice stem borers or rice leaf folders, comprising stably integrated in its genome, the chimeric gene of claim 7.

33. The rice plant of claim 32, wherein said rice plant is resistant to *Chilo suppressalis, Marasmia patnalis, Scirpophaga incertulas* or *Cnaphalocrocis medinalis.*

34. A method for controlling Lepidopteran plant insect pests comprising planting or sowing in a field, plants comprising the DNA of claim 7.

35. A method for controlling Lepidopteran plant insect pests comprising expressing the DNA of claim 7 in rice plants.

36. The method of claim 34, wherein said Lepidopteran plant insect pests are rice stem borers or rice leaf folders.

37. The method of claim 34, wherein said Cry1Ab protein comprises the amino acid sequence of SEQ ID No. 12 from amino acid position 30 to amino acid position 617.

38. The method of claim 35, wherein said Lepidopteran plant insect pests are rice stem borers or rice leaf folders.

39. The method of claim 25, wherein said Lepidopteran plant insect pests are rice stem borers or rice leaf folders.

40. A process for obtaining a rice plant and progeny thereof resistant to *Chilo suppressalis, Marasmia patnalis, Cnaphalocrocis medinalis*, or *Scirpophaga incertulas*, comprising transforming a rice plant with the DNA of claim 7.

41. A method of producing plants or seeds resistant to insects, comprising the steps of:

(a) obtaining a plant transformed with the DNA of claim 7, and (b) selecting progeny of said plant, or seeds thereof containing said DNA, using specific primers or probes.

42. A microorganism comprising the DNA of claim 7.

43. The microorganism of claim 42, which is of the genus *Escherichia, Bacillus* or *Agrobacterium*.

* * * * *